(12) United States Patent
Kubota et al.

(10) Patent No.: US 9,224,080 B2
(45) Date of Patent: Dec. 29, 2015

(54) SPECTRAL CHARACTERISTIC ACQUISITION DEVICE, IMAGE EVALUATION DEVICE, AND IMAGE FORMATION APPARATUS

(71) Applicants: Yoichi Kubota, Tokyo (JP); Kohei Shimbo, Kanagawa (JP); Naohiro Kamijo, Kanagawa (JP)

(72) Inventors: Yoichi Kubota, Tokyo (JP); Kohei Shimbo, Kanagawa (JP); Naohiro Kamijo, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/614,497

(22) Filed: Feb. 5, 2015

(65) Prior Publication Data

US 2015/0235114 A1 Aug. 20, 2015

(30) Foreign Application Priority Data

Feb. 20, 2014 (JP) .................. 2014-030270
May 13, 2014 (JP) .................. 2014-099572
Dec. 17, 2014 (JP) .................. 2014-255400

(51) Int. Cl.
*H04N 1/60* (2006.01)
*G06K 15/02* (2006.01)

(52) U.S. Cl.
CPC .......... *G06K 15/1878* (2013.01); *G06K 15/027* (2013.01); *H04N 1/6027* (2013.01); *H04N 1/6041* (2013.01); *H04N 1/6044* (2013.01); *H04N 1/6097* (2013.01)

(58) Field of Classification Search
None
See application file for complete search history.

(56) References Cited

U.S. PATENT DOCUMENTS

| | | |
|---|---|---|
| 5,933,520 A | 8/1999 | Ishimoto et al. |
| 6,876,448 B2 | 4/2005 | Imura et al. |
| 6,975,949 B2 | 12/2005 | Mestha et al. |
| 7,671,992 B2 | 3/2010 | Ehbets et al. |
| 8,497,988 B2 | 7/2013 | Shimbo et al. |
| 8,559,005 B2 | 10/2013 | Shimbo et al. |
| 8,755,046 B2 | 6/2014 | Shimbo et al. |
| 8,755,701 B2 | 6/2014 | Hyoki |
| 8,879,057 B2 | 11/2014 | Shimbo et al. |
| 2011/0063615 A1 | 3/2011 | Shimbo et al. |

(Continued)

FOREIGN PATENT DOCUMENTS

| | | |
|---|---|---|
| EP | 0301506 | 2/1989 |
| JP | 2002-310799 | 10/2002 |

(Continued)

OTHER PUBLICATIONS

Norimichi Tsumura et al., "Estimation of Spectral Reflectances from Multi-Band Images by Multiple Regression Analysis", Japanese Journal of Optics vol. 27 No. 7, pp. 384-391 (1998).

(Continued)

*Primary Examiner* — Scott A Rogers
(74) *Attorney, Agent, or Firm* — IPUSA, PLLC

(57) ABSTRACT

A spectral characteristic acquisition device includes a light irradiation part configured to irradiate an object with light, a diffraction part configured to diffract light reflected from the object to provide diffracted light, a light-receiving part configured to receive the diffracted light and output a signal based on an amount of the diffracted light, a calibration color index configured to include a color with a known spectral characteristic, and an operation part configured to calculate a spectral characteristic of the object from a signal output from the light-receiving part by using a predetermined transformation matrix and calibrate the transformation matrix by using the calibration color index.

10 Claims, 22 Drawing Sheets

(56) References Cited

U.S. PATENT DOCUMENTS

| | | | |
|---|---|---|---|
| 2011/0299104 A1 | 12/2011 | Seo et al. | |
| 2012/0182373 A1 | 7/2012 | Hayashi | |
| 2013/0063723 A1* | 3/2013 | Shimbo | B41F 33/00 356/328 |
| 2013/0235376 A1 | 9/2013 | Kamijo et al. | |
| 2014/0333927 A1 | 11/2014 | Shimbo et al. | |
| 2015/0049371 A1* | 2/2015 | Kamijo | H04N 1/00015 358/504 |

FOREIGN PATENT DOCUMENTS

| | | |
|---|---|---|
| JP | 2003-139702 | 5/2003 |
| JP | 3566334 | 9/2004 |
| JP | 2005-315883 | 11/2005 |
| JP | 3925301 | 6/2007 |
| JP | 2008-518218 | 5/2008 |
| JP | 2008-304205 | 12/2008 |
| JP | 2010-256324 | 11/2010 |
| JP | 2012-070023 | 4/2012 |
| JP | 2012-154711 | 8/2012 |
| JP | 2012-229922 | 11/2012 |

OTHER PUBLICATIONS

U.S. Appl. No. 14/454,847, filed Aug. 8, 2014.
Office Action dated May 4, 2015 issued to related U.S. Appl. No. 14/454,847.
Extended European Search Report dated Aug. 6, 2015.

* cited by examiner

SPECTRAL CHARACTERISTIC ACQUISITION DEVICE, IMAGE EVALUATION DEVICE, AND IMAGE FORMATION APPARATUS

BACKGROUND OF THE INVENTION

1. Field of the Invention

An aspect of the present invention relates to at least one of a spectral characteristic acquisition device, an image evaluation device, and an image formation apparatus.

2. Description of the Related Art

In an image formation apparatus such as a printing apparatus or a printer, one of important technical problems is a control of color tone such as color stability or color reproducibility. In recent years, an image formation apparatus has been realized that installs a spectrometer such as a spectrophotometer for a control of color tone.

In such an image formation apparatus, a colorimetric value such as XYZ or L*a*b* defined in CIE (International Commission on Illumination) is obtained from a spectral characteristic of diffused or reflected light from a print surface as measured by a spectrometer to execute check of color tone of a print or adjustment of an image formation process.

For example, a spectrometer for measuring visible light detects light in a wavelength range of 400-700 nm for each wavelength band with a pitch of 10 nm and outputs 31 or more digitized values. A measurement of a spectral characteristic needs a certain period of time because diffused or reflected from a surface to be measured is temporally and spatially divided into 31 or more to acquire a light intensity signal. Therefore, for example, in a case where an in-line measurement is executed for an output image at a rate corresponding to a printing speed thereof in an image formation apparatus for executing high-speed printing, a rate of detection may be insufficient so that application thereof may be difficult.

Then, in a case where a spectral characteristic of a measurement object with a comparatively smoothly changed spectral characteristic distribution, such as a printed image, is measured, for example, a method has been known that detects light in a comparatively few or about 3-16 wavelength bands referred to as a multiband by a spectrometer and estimates a spectral characteristic of a measurement object from a detection result thereof (for example, see Norimichi Tsumura, Hideaki Haneishi, Youichi Miyake, "Estimation of Spectral Reflectances from Multi-Band Images by Multiple Regression Analysis", Japanese Journal of Optics, Vol. 27, No. 7, pp. 384-391 (1998)).

According to such a method, it is possible to reduce a period of time necessary for detection because the number of wavelength bands to be detected is small, and it is also possible to be applied to a field required for a high-speed measurement such as an in-line measurement for a printed image. Furthermore, for example, it is possible to estimate, at high precision, a spectral characteristic of a measurement object provided in such a manner that it is possible to acquire statistical information with respect to a spectral characteristic thereof preliminarily, such as a printed image with a color reproduced by a combination of about 4 kinds of color materials.

For example, estimation of a spectral characteristic is executed by using a transformation matrix that is obtained from a measurement result for a standard sample with a known spectral characteristic. It is preferable for a transformation matrix to be obtained from a standard sample that has a feature approximating a spectral characteristic of a measurement object, in order to estimate such a spectral characteristic at high precision. Furthermore, it is preferable to set a plurality of transformation matrices dependent on a feature of a measurement object or the like in such a manner that it is possible to handle a variety of measurement objects. However, it is necessary to prepare and measure an enormous number of standard samples and execute an operation process thereof in order to obtain a plurality of transformation matrices, so that a lot of labor and coat is required.

Then, a method has been disclosed that produces, by calculation, a large amount of learning data to be used for calculation of a transformation matrix and obtains a transformation matrix based on the learning data obtained by the calculation instead of practically measuring a standard sample (for example, see Japanese Patent Application Publication No. 2012-154711).

However, in the method as described above, there is a possibility that an estimation error or a calculation error is included in learning data produced by calculation and these errors also influence a transformation matrix to be obtained based on the learning data so that precision of estimation of a spectral characteristic is lowered.

SUMMARY OF THE INVENTION

According to one aspect of the present invention, there is provided a spectral characteristic acquisition device, including a light irradiation part configured to irradiate an object with light, a diffraction part configured to diffract light reflected from the object to provide diffracted light, a light-receiving part configured to receive the diffracted light and output a signal based on an amount of the diffracted light, a calibration color index configured to include a color with a known spectral characteristic, and an operation part configured to calculate a spectral characteristic of the object from a signal output from the light-receiving part by using a predetermined transformation matrix and calibrate the transformation matrix by using the calibration color index.

According to another aspect of the present invention, there is provided an image evaluation device, including the spectral characteristic acquisition device as described above, and an image evaluation part configured to evaluate an image formed on the object based on a spectral characteristic of the object acquired by the spectral characteristic acquisition device.

According to another aspect of the present invention, there is provided an image formation apparatus, including an image formation device configured to form an image on the object, and the image evaluation device as described above.

DETAILED DESCRIPTION OF THE PREFERRED EMBODIMENTS

Embodiments for implementing the invention will be described below, with reference to the drawings. In each drawing, an identical numeral or letter may be attached to an identical component to omit a redundant description thereof. Here, a spectral characteristic in the present application refers to an amount of light for diffused or reflected light being represented as a function of a wavelength thereof and includes a spectral reflectance distribution.

A First Embodiment

<A Configuration of a Spectral Characteristic Acquisition Device>

Figure 1:
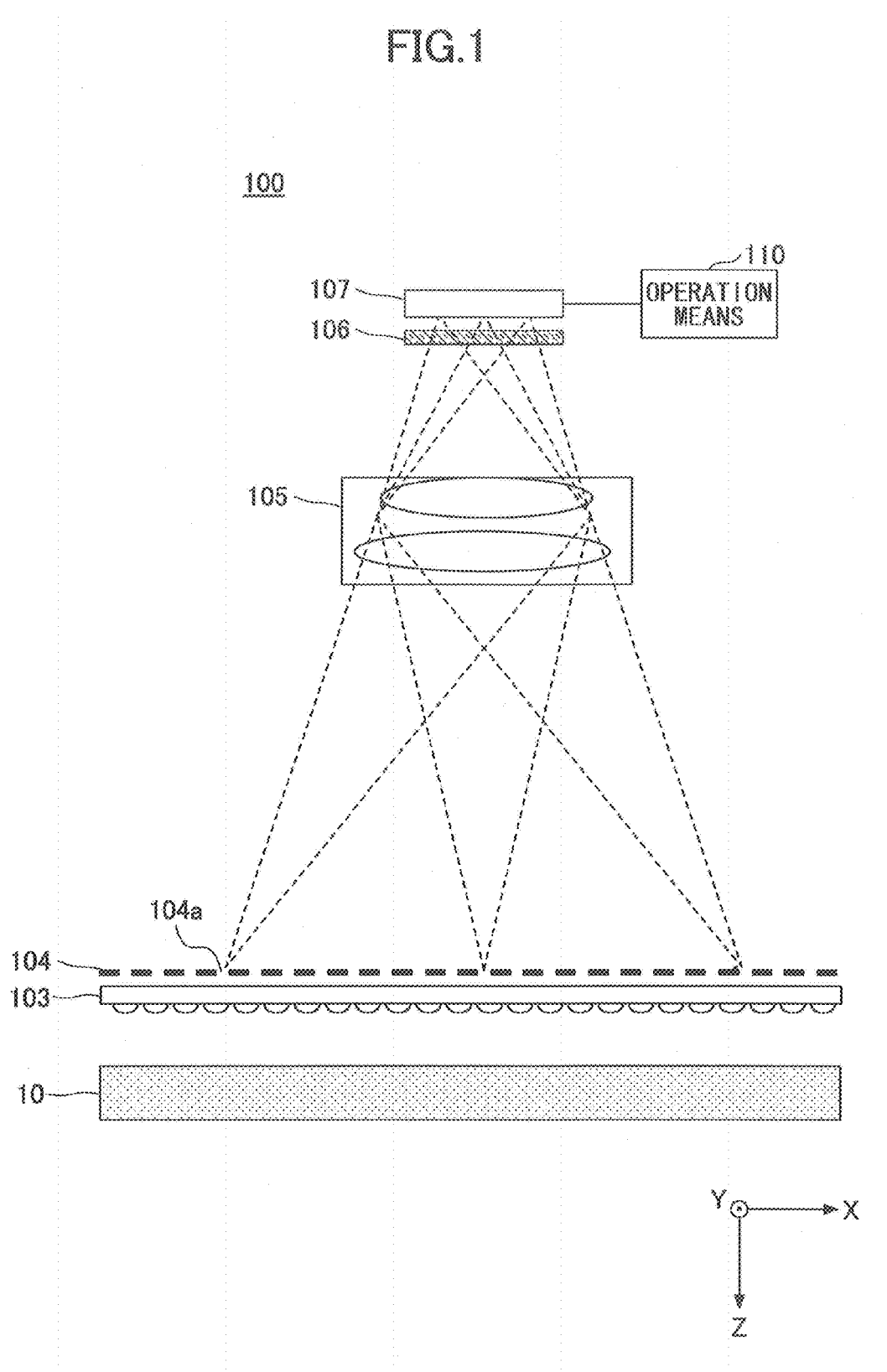
FIG. 1 is a front view that illustrates a general configuration of a spectral characteristic acquisition device according to a first embodiment.
Figure 2:
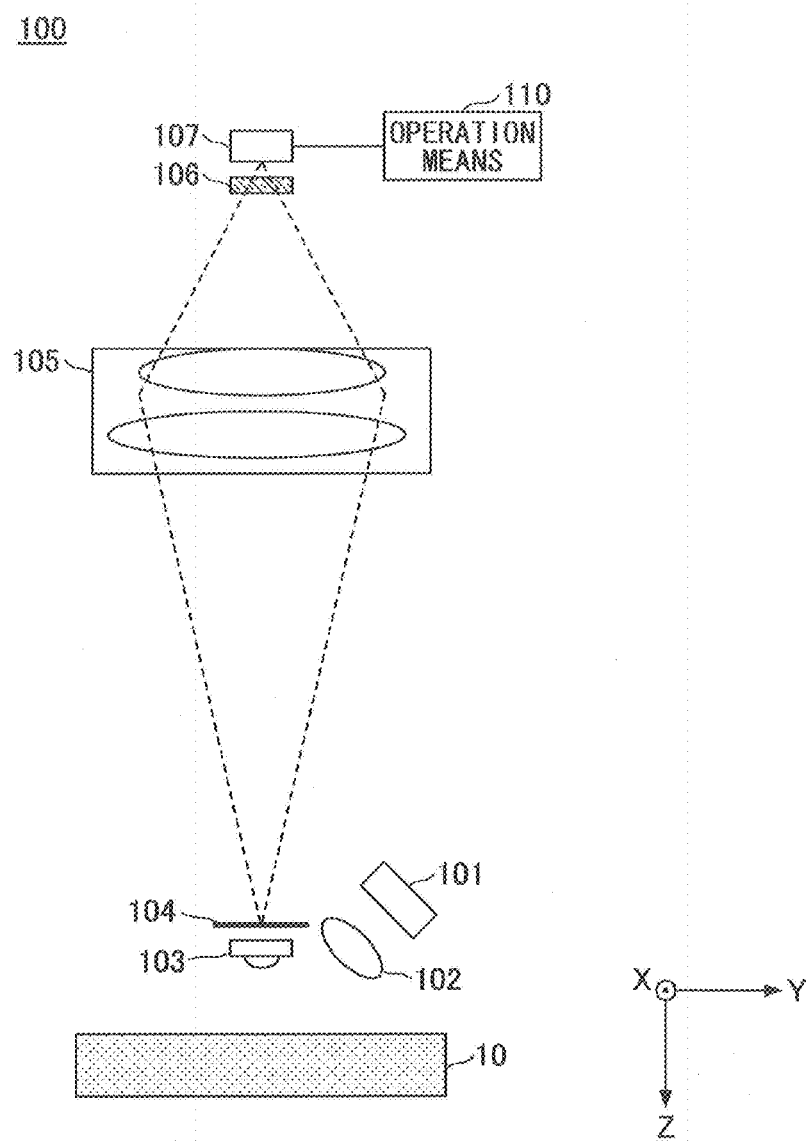
FIG. 2 is a side view that illustrates a general configuration of a spectral characteristic acquisition device according to a first embodiment.

FIG. 1 and FIG. 2 illustrate a configuration example of a spectral characteristic acquisition device 100 according to first embodiment. FIG. 1 is a front view of the spectral characteristic acquisition device 100 and FIG. 2 is a side view of the spectral characteristic acquisition device 100. In the following descriptions, an X-direction indicates a direction of alignment of pixels of a line sensor 107 that is a light-receiving means, a Y-direction indicates a direction orthogonal to the direction of alignment of pixels on a light-receiving surface of the line sensor 107, and a Z-direction indicates a direction orthogonal to the direction of alignment of pixels of the line sensor 107 and perpendicular to the light-receiving surface. Here, broken lines illustrated in FIG. 1 and FIG. 2 schematically illustrates a representative light paths after diffusion or reflection of light that irradiates a measurement object (an object) 10.

The spectral characteristic acquisition device 100 a line illumination light source 101 and a collimator lens 102 (non-illustrated in FIG. 1), as a light irradiation means, a micro-lens array 103, a hole array 104, an imaging optical system 105, a diffraction element 106 as a diffraction means, the line sensor 107 as a light-receiving means, and an operation means 110.

The line illumination light source 101 and the collimator lens 102 irradiate the measurement object 10 with a spectral characteristic to be measured, with line-shaped light spreading in a width direction (X-direction). For example, the measurement object 10 is a recording medium with an image formed on a surface thereof or the like.

For example, the line illumination light source 101 is a white Light Emitting Diode (LED) array that has an intensity with respect to approximately a gamut of visible light. For example, the line illumination light source 101 may be a fluorescent lamp such as a cold-cathode tube, a lamp light source, or the like. However, it is preferable for the line illumination light source 101 to emit light with respect to a wavelength region necessary for spectrometry and to be capable of homogeneously illuminating an entire measurement area.

The collimator lens 102 collimates (as generally collimated light) or condenses, and irradiates the measurement object 10 with, light emitted from the line illumination light source 101. Although a configuration example that has the line illumination light source 101 and the collimator lens 102 is illustrated as a light irradiation means, a configuration may be provided in such a manner that the collimator lens 102 is omitted.

The micro-lens array 103 images light diffused or reflected from the measurement object 10 irradiated with light onto the hole array 104. However, accurate imaging onto the hole array 104 is not necessarily required, and a defocussed state or an infinite system may be provided. Furthermore, for example, a fist imaging means may be a gradient-index-type lens array such as a Selfoc (registered trademark) lens array or an imaging optical system composed of a plurality of lenses or mirrors, instead of the micro-lens array 103.

The hole array 104 is such that a plurality of apertures 104a are formed in line in an X-direction as illustrated in FIG. 1. The hole array 104 is such that a part other than the apertures 104a are a light-blocking part that blocks light, and light imaged by the micro-lens array 103 onto the hole array 104 transmits through the apertures 104a to the imaging optical system 105. For example, the hole array 104 may be a metal or black resin material with the apertures 104a formed thereon, a glass, a transparent resin, or the like, with a metallic film, a black resin, or the like, patterned and applied thereon, or the like. Furthermore, a plurality of apertures may be aligned in two or more lines.

The imaging optical system 105 are composed of a plurality of lenses and images light that has transmitted through the hole array 104, through the diffraction element 106 onto a light-receiving surface of the line sensor 107. For example, the imaging optical system 105 may be lenses used for a general scanner optical system, or industrially used lenses for line sensor.

An optical system for the spectral characteristic acquisition device 100 according to the present embodiment is a so-called 45/0 optical system in such a manner that illumination light emitted from the line illumination light source 101 is obliquely incident on the measurement object 10 at about 45 degrees and the line sensor 170 receives light diffused or reflected from the measurement object 10 in a Z-direction, as illustrated in FIG. 2. Here, an optical system for the spectral characteristic acquisition device 100 may be a so-called 0/45 optical system in such a manner that illumination light emitted from the line illumination light source 10 is perpendicularly incident on the measurement object 10 and the line sensor 107 receives light diffused or reflected from the measurement object 10 in a direction at 45 degrees, or the like.

The line sensor 107 is one example of a light-receiving means, is composed of a plurality of pixels, and outputs an electric signal that corresponds to incident light diffracted or reflected from the diffraction element 106 for each of different wavelength bands. For example, the line sensor 107 is a Metal Oxide Semiconductor (MOS) Device, a Complementary Metal Oxide Semiconductor (CMOS) Device, a Charge Coupled Device (CCD), a Photo-Diode Array (PDA), or the like.

Figure 3:
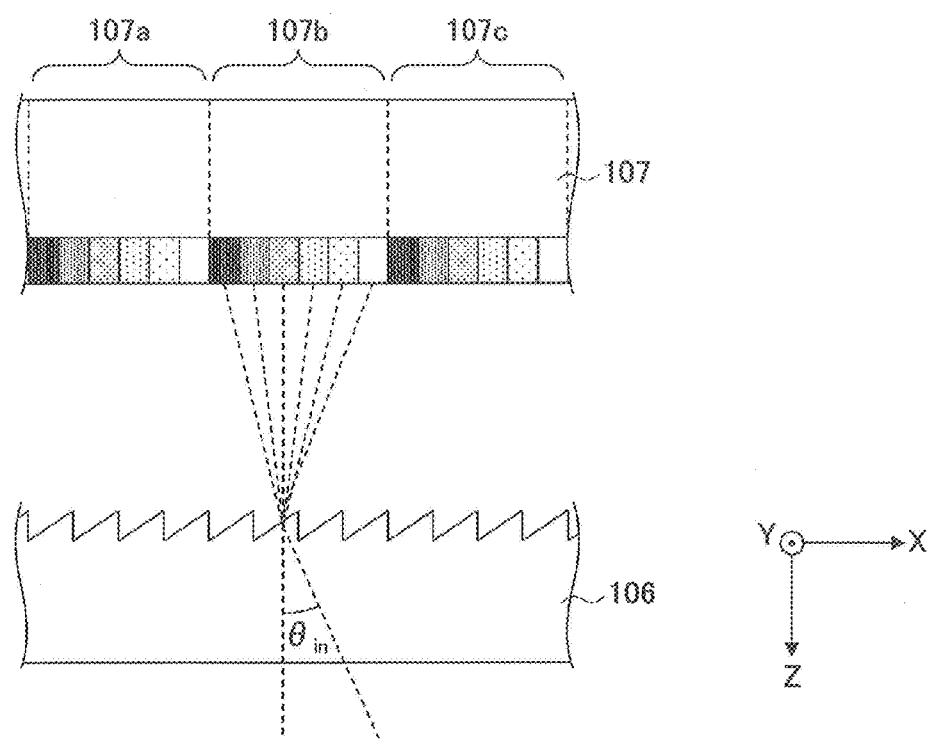
FIG. 3 is a diagram that schematically illustrates a pixel structure of a line sensor in a first embodiment.

FIG. 3 is a diagram that schematically illustrates a pixel structure of the line sensor 107. As illustrated in FIG. 3, the line sensor 107 has a pixel structure wherein a plurality of pixels are aligned in a line in an X-direction. The line sensor 107 is a spectral sensor array wherein a first spectral sensor 107a, a second spectral sensor 107b, a third spectral sensor 107c, and the like (a plurality thereof) are further aligned wherein n pixels are provided as one group. Each of the first spectral sensor 107a, the second spectral sensor 107b, the third spectral sensor 107c, and the like has N pixels and receives light of a diffraction image different from one another. Here, a plurality of pixels that are had by the line sensor 107 are not limited to a structure of pixels aligned in a line but may be aligned in two or more lines.

An aperture 104a of the hole array 104 and N pixels of a spectral sensor of the line sensor 107 have an imaging relationship in such a manner that light that has transmitted through one aperture 104a of the hole array 104 is incident on N pixels that are had by one spectral sensor of the line sensor 107.

The diffraction element 106 is such that a saw-tooth shape as illustrated in FIG. 3 is formed on a transparent substrate at a predetermined interval. For example, a saw-tooth portion of the diffraction element 106 may be another shape such as a step shape.

Herein, as p is a period of a saw-tooth shape of the diffraction element 106, light with a wavelength λ incident on the diffraction element 106 at an angle θin is diffracted at an angle θm that is represented by formula (1):

$$\sin\theta_m = m\frac{\lambda}{p} + \sin\theta_{in}. \quad (1)$$

In formula (1), m is an order of diffraction that is caused by the diffraction element 106, wherein it is possible to be a positive or negative integer value.

It is possible to provide light with different wavelength bands incident on N pixels in accordance with a wavelength dependency of a diffraction angle θm that is represented by formula (1).

Herein, light diffracted by the diffraction element 106 may be such that 0th order light, a 2nd order diffraction image, a diffraction image that has transmitted through an adjacent aperture, or the like overlaps on a light-receiving surface of the line sensor 107. In such a case, crosstalk is caused so that acquisition of an accurate spectral characteristic is difficult.

Herein, for example, a configuration is provided in such a manner that the diffraction element 106 is rotated in an XY-plane or an angle of a tooth of the diffraction element 106 is set appropriately so that a diffraction direction of diffracted light and a direction of pixel alignment of the line sensor 107 have a predetermined angle α.

Figure 4:
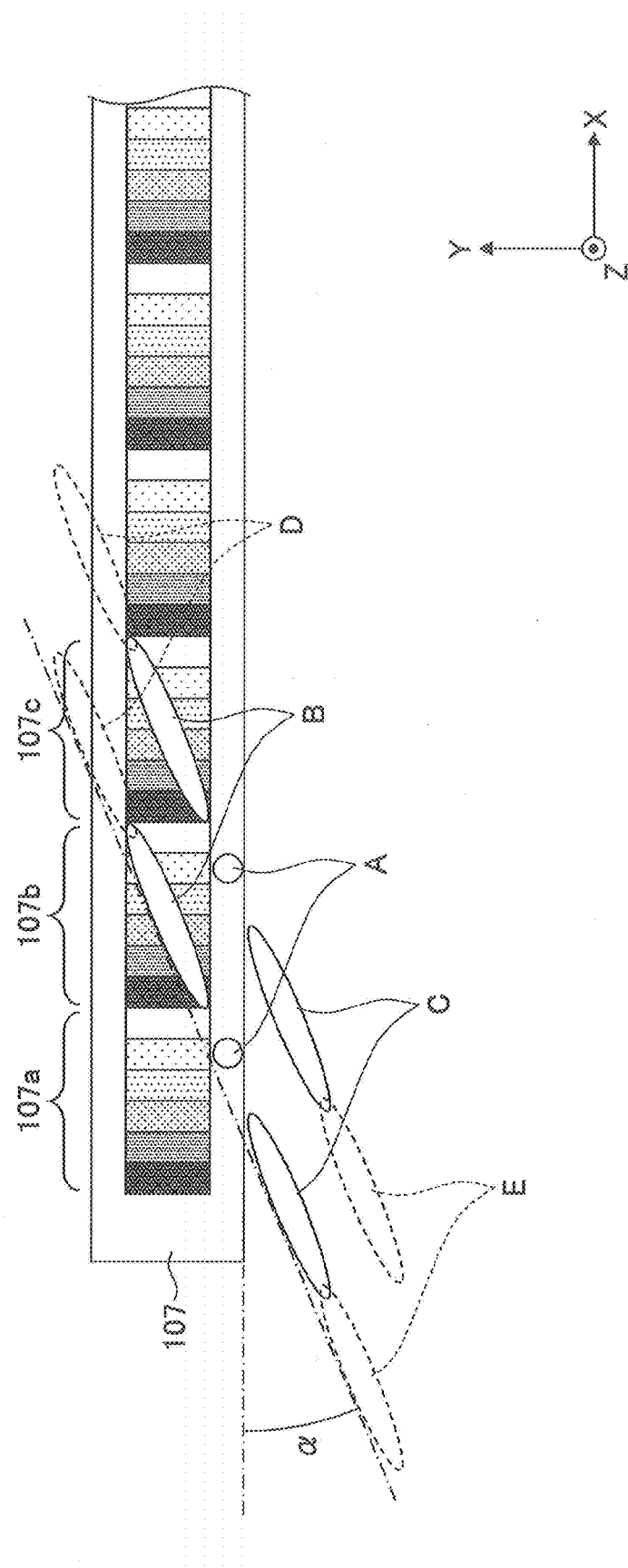
FIG. 4 is a diagram that explains a relationship between a liner sensor and a diffraction image in a first embodiment.

In such a configuration, a diffraction image is incident so as to have or incline by an angle α with respect to a direction of pixel alignment of the line sensor 107 as illustrated in FIG. 4, so that crosstalk caused by overlapping of diffraction images is prevented. In the present embodiment, only a +1st order diffraction image B for each aperture of the hole array 104 is imaged on the line sensor 107 while an unrequired non-diffraction image A (0th order diffraction image), a −1st order diffraction image C, a +2nd order diffraction image D, a −2nd order diffraction image E, and the like, are imaged at positions distant from pixels of the line sensor 107. Thus, the spectral characteristic acquisition device 100 excludes crosstalk among diffraction images, wherein it is possible to obtain a spectral characteristic of the measurement object 10 from a +1st order diffraction image B. Here, a +1st order diffraction image B may simply be referred to as a diffraction image in the following descriptions.

The operation means 110 estimates and calculates a spectral characteristic of the measurement object 10, from an electric signal that is outputted from the line sensor 107, by using a transformation matrix. For example, the operation means 110 includes a CPU, a ROM, a main memory, and the like, wherein a program recorded in the ROM or the like is read out in the main memory and executed by the CPU to realize a function. Here, the operation means 110 may be physically composed of a plurality of devices.

Figure 5:
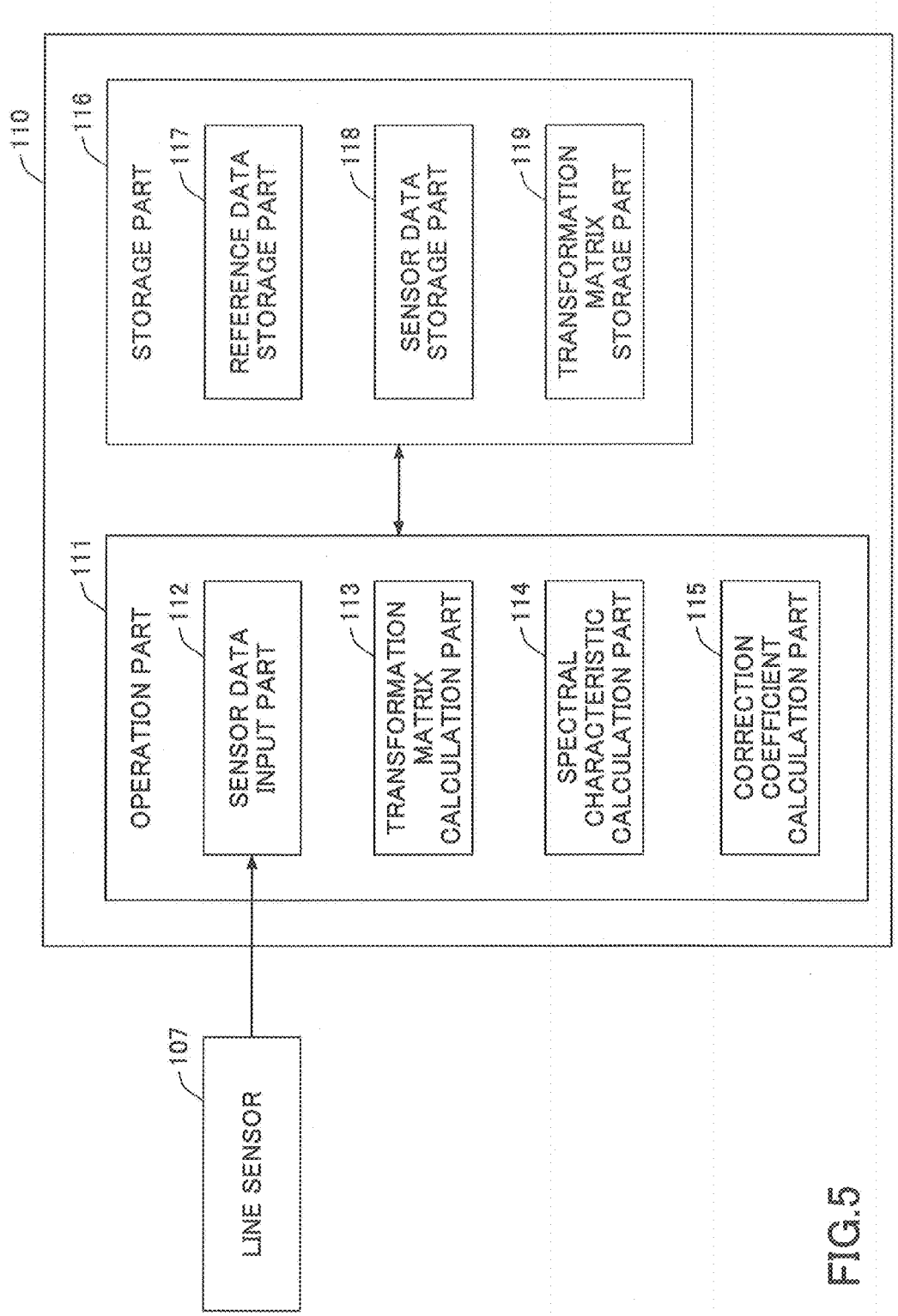
FIG. 5 is a diagram that illustrates a functional configuration of an operation means in a first embodiment.

FIG. 5 is a diagram that illustrates a functional configuration of the operation means 110 in the first embodiment.

As illustrated in FIG. 5, the operation means 110 has an operation part 111 that has a sensor data input part 112, a transformation matrix calculation part 113 as a transformation matrix correction means, a spectral characteristic calculation part 114 as a spectral characteristic calculation means, and a correction coefficient calculation part 115 as a first correction coefficient calculation means or a second correction coefficient calculation means, and a storage part 116 that has a reference data storage part 117, a sensor data storage part 118, and a transformation matrix storage part 119. A function of each part that is had by the operation means 110 will be described below, and a method will be described that estimates and calculates a spectral reflectance distribution as a spectral characteristic of the measurement object 10.

As the measurement object 10 is irradiated with light from the line illumination light source 101 in the spectral characteristic acquisition device 100, an electric signal is outputted from each spectral sensor of the line sensor 107 that has received light of a diffraction image and is inputted into the sensor data input part 112 of the operation means 110 as sensor data.

As sensor data is inputted into the sensor data input part 112, the spectral characteristic calculation part 114 calculates a spectral characteristic of the measurement object 10 from the sensor data by using a transformation matrix that is preliminarily stored in the transformation matrix storage part 119.

(Estimation of a Spectral Characteristic)

A method will be described that estimates and calculates a spectral reflectance distribution as a spectral characteristic from sensor data for one spectral sensor of the line sensor 107 in the spectral characteristic calculation part 114 in the present embodiment. Here, a spectral characteristic may be obtained by a method that is different from a method that will be described below.

As a matrix v that stores sensor data vi (i=1−N) from N pixels that constitute one spectral sensor of the line sensor 107 and a transformation matrix G are used, a matrix r that stores a spectral reflectance with respect to each wavelength band (for example, 31 in 400-700 nm at a pitch of 10 nm) is represented by the following formula (2):

$$r = Gv. \quad (2)$$

A transformation matrix G is obtained from a matrix R that stores spectral reflectance distributions of a plurality of (n) standard samples that are known and a matrix V that stores signal outputs v that are obtained from a spectral sensor and the standard samples, wherein a square norm of an error $\|\ldots\|^2$ is minimizes by using a least square method, as illustrated in the following formulas (3)-(5):

$$R = [r1, r2, \ldots, rn] \quad (3)$$

$$V = [v1, v2, \ldots, vn] \quad (4)$$

$$e = \|R - GV\|^2 \rightarrow \min \quad (5)$$

For example, a regression transformation matrix G of a regression equation from V to R, wherein V is an explanatory variable and R is a response variable, is obtained by using a generalized inverse matrix of Moore-Penrose that gives a square minimum norm solution of a matrix V, in accordance with the following formula (6):

$$G = RV^T(VV^T)^{-1} \quad (6)$$

In formula (6), a superscript T denotes transposition of a matrix and a superscript −1 denotes an inverse matrix.

Figure 6:
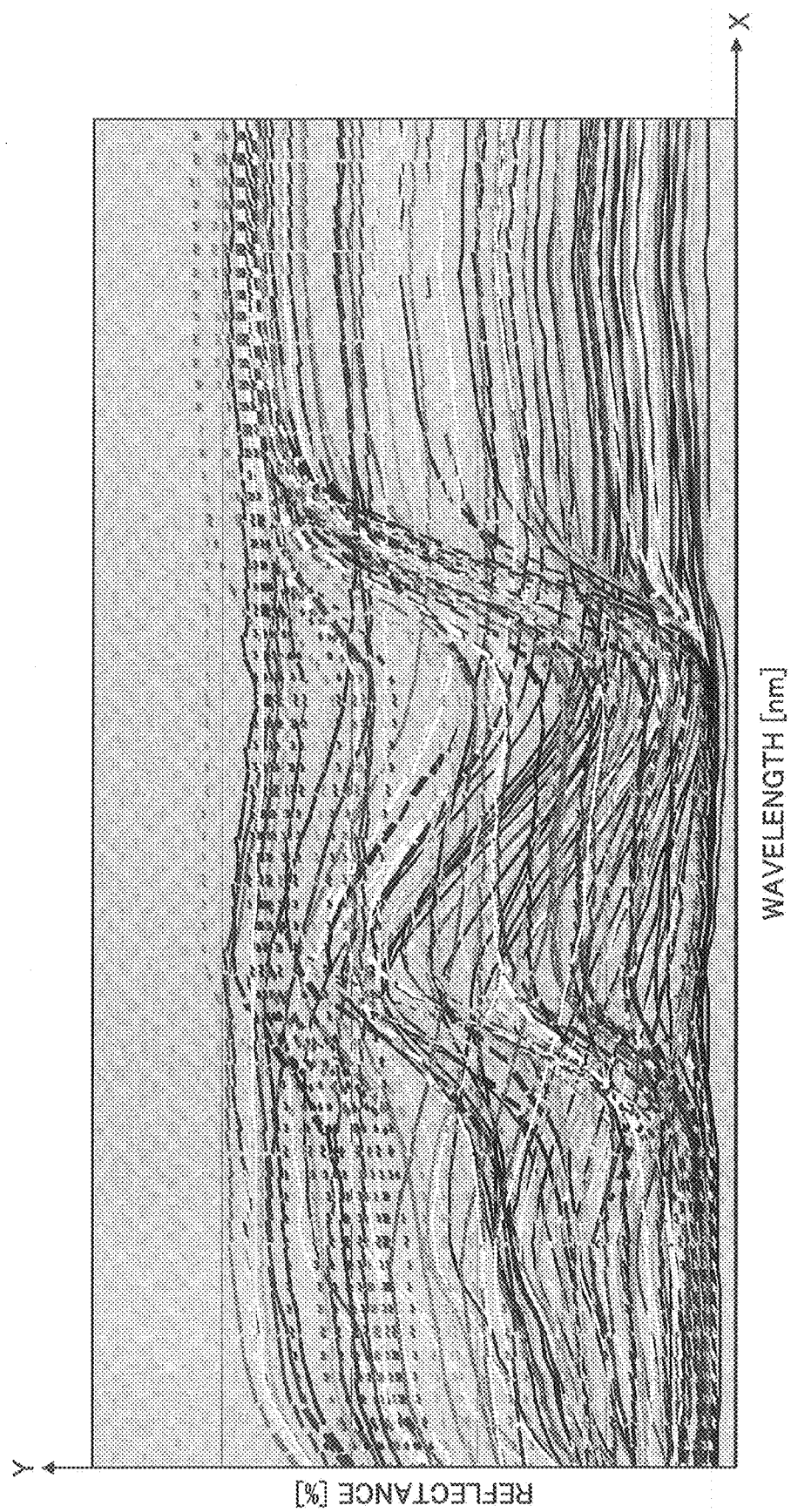
FIG. 6 is a diagram that illustrates a measurement result of a spectral reflectance distribution of a standard sample.

FIG. 6 illustrates a result of spectral reflectance of a plurality of standard samples with different colors that are measured with respect to wavelengths 400-700 nm at an interval of 10 nm by using a high-precision spectrometer. In the spectral characteristic acquisition device 100, a result of measurement of a spectral reflectance of a standard sample is preliminarily stored in the reference data storage part 117 of the operation means 110.

The transformation matrix calculation part 113 produces a matrix $V_{ref}$ based on sensor data that are obtained from a standard sample in the spectral characteristic acquisition device 100. Furthermore, a matrix $R_{ref}$ is produced from a spectral reflectance distribution of a standard sample that is stored in the reference data storage part 117. The transformation matrix calculation part 114 calculates a transformation matrix G from thus produced $V_{ref}$ and $R_{ref}$ based on formula (6).

A transformation matrix G calculated by the transformation matrix calculation part 113 is stored in the transformation matrix storage part 119. Furthermore, a matrix Vref of sensor data that is obtained from a standard sample in the spectral characteristic acquisition device 100 is stored in the sensor data storage part 118 of the operation means 110.

In a case where a spectral characteristic of the measurement object 10 is estimated, the spectral characteristic calculation part 114 first acquires a matrix $V_{exp}$ from sensor data for the measurement object 10 and a transformation matrix G stored in the transformation matrix storage part 119. Then, it is possible for the spectral characteristic calculation part 114 to obtain a spectral reflectance $R_{exp}$ of the measurement object 10 by estimation using a matrix $V_{exp}$ and a transformation matrix G and based on formula (2).

Herein, a spectral characteristic of a toner image outputted from an electrophotographic image formation apparatus was estimated by using the spectral characteristic acquisition device 100 and simulation was executed that calculated a color difference that was an estimation error, from an estimated spectral characteristic. In simulation, obtained were a colorimetric result in a case where the number N of pixels of a spectral sensor that was had by the line sensor 107 was changed and a color difference (ΔE) from a colorimetric result obtained from a higher-precision spectrometer.

Figure 7:
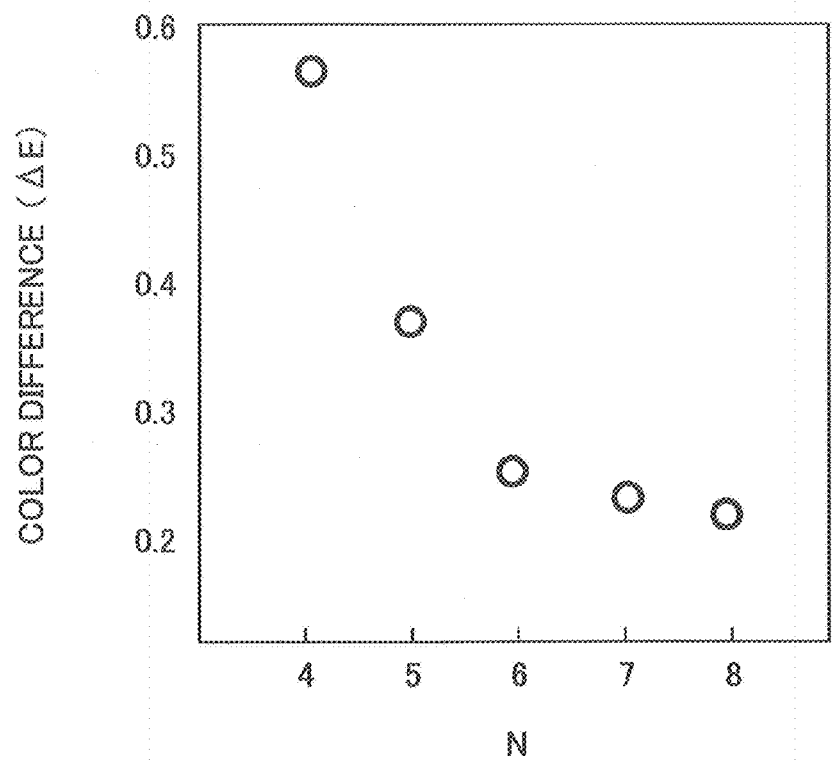
FIG. 7 is a diagram that illustrates a simulation result.

FIG. 7 is a diagram that illustrates a result of simulation. From a result as illustrated in FIG. 7, it is possible to find that a color difference (ΔE) is decreased as the number N of pixels of a spectral sensor is increased, so that a spectral characteristic is desired at a high precision.

In estimation and calculation as described above, for example, it is desirable for a plurality of reference samples that are used for calculation of a transformation matrix G to be homogenously selected from a reproducible color range (gamut) for a printed image in a color space of an XYZ color system, an L*a*b* color system, or the like. As a transformation matrix G is used that is calculated based on thus selected reference sample, for example, it is possible to estimate a spectral characteristic of a printed image that is had by the measurement object 10, at high precision.

However, it takes a lot of time and cost to create, maintain, and measure a reference sample. Therefore, it is desirable for a transformation matrix G to be obtained based on a few number of reference samples as long as it is possible to retain precision of estimation of a spectral characteristic.

Figure 8:
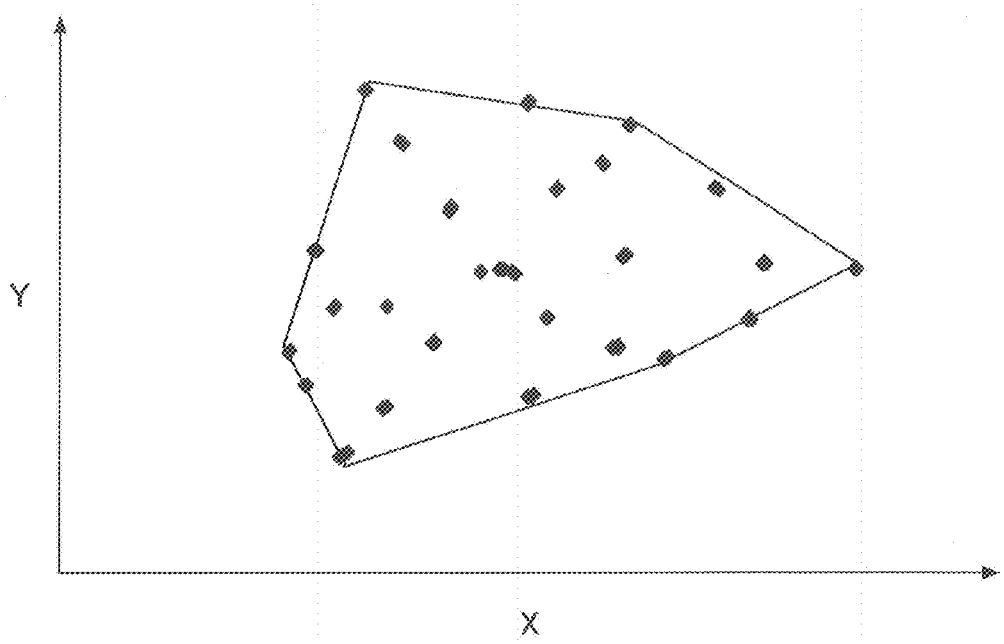
FIG. 8 is a diagram that illustrates an XY chromaticity distribution of a reference sample and a color reproduction range of a toner image.

In the present embodiment, toner images with 27 colors that are homogenously selected from a reproducible color range of an electrophotographic image formation apparatus are used as reference samples. FIG. 8 is a diagram that illustrates an XY chromaticity of each of reference samples with 27 colors, wherein each point indicates an XY chromaticity of a reference sample and a solid line indicates a reproducible color range of a toner image. As illustrated in FIG. 8, it is possible to find that reference samples in the present embodiment are homogeneously selected from a reproducible color range of a toner image.

In the spectral characteristic acquisition device 100, a transformation matrix G that is calculated by using thus selected reference sample in the transformation matrix calculation part 113 is preliminarily stored in the transformation matrix storage part 119.

(Calibration of a Transformation Matrix)

Figure 9:
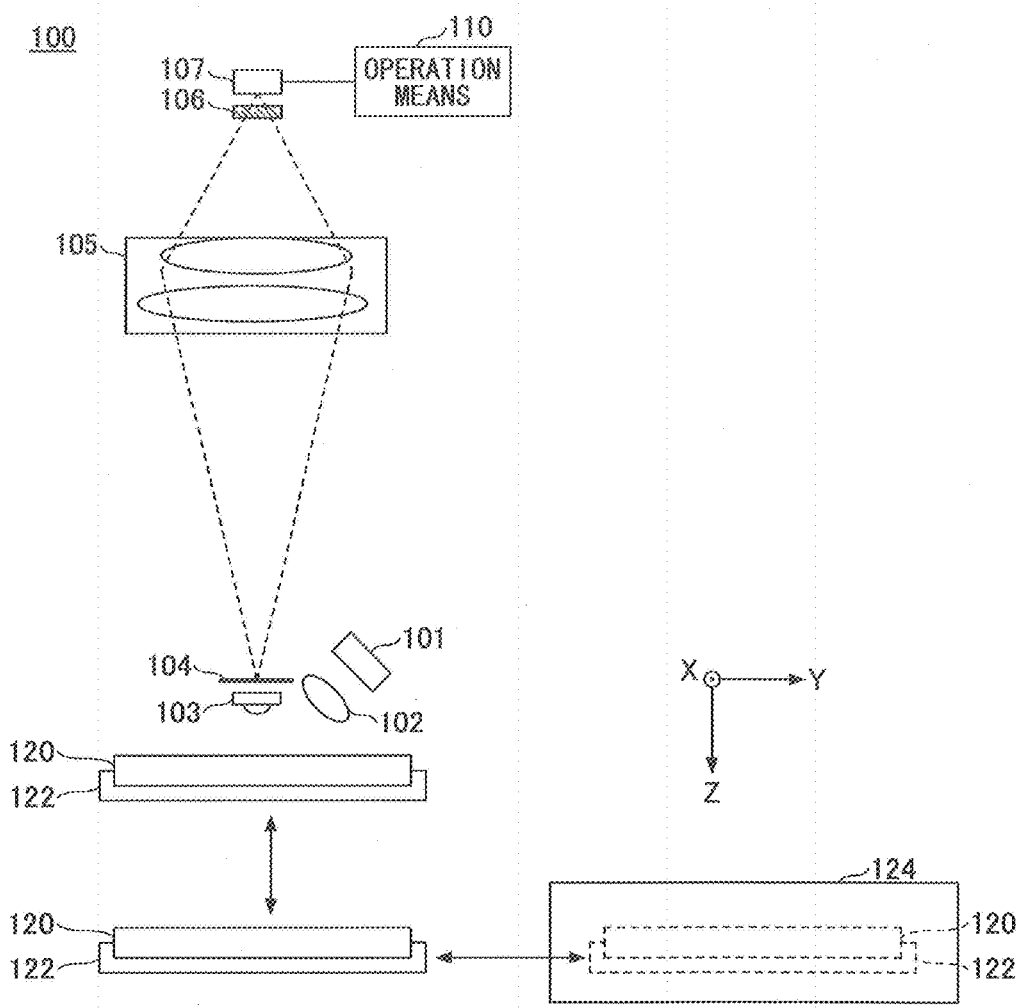
FIG. 9 is a side view that illustrates a general configuration of a spectral characteristic acquisition device that includes a calibration unit.

Herein, the spectral characteristic acquisition device 100 according to the present embodiment is provided with a calibration unit 120 as a calibration color index that is used for calibration of a transformation matrix G calculated by using a reference sample, as illustrated in FIG. 9. The transformation matrix calculation part 113 in the spectral characteristic acquisition device 100 has a function of calibrating a transformation matrix stored in the transformation matrix storage part 119 by using sensor data of the line sensor 107 that is obtained from a color index provided for the calibration unit 120, as a transformation matrix calibration means.

Figure 10:
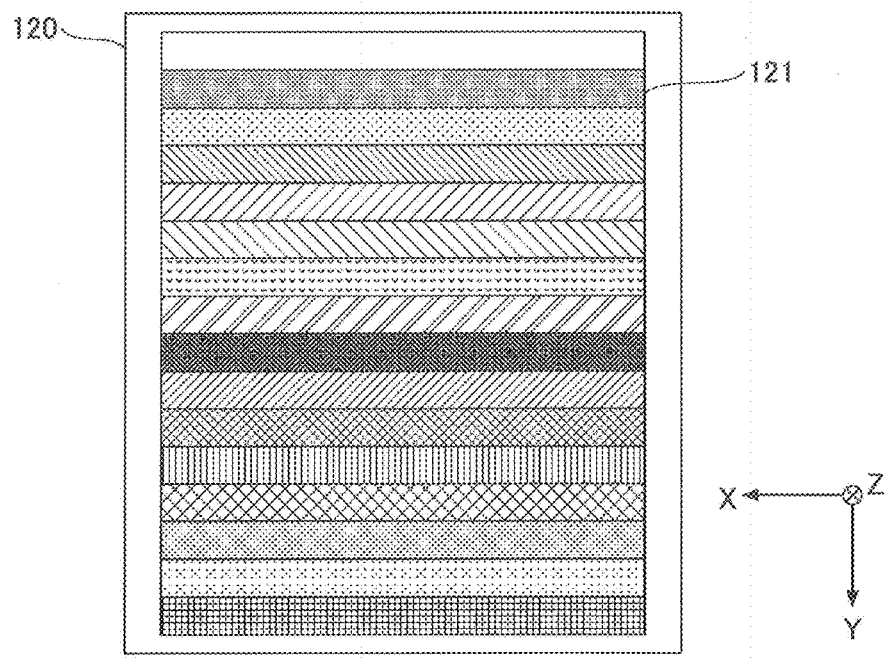
FIG. 10 is a plan view that illustrates a general configuration of a calibration unit.
Figure 11:
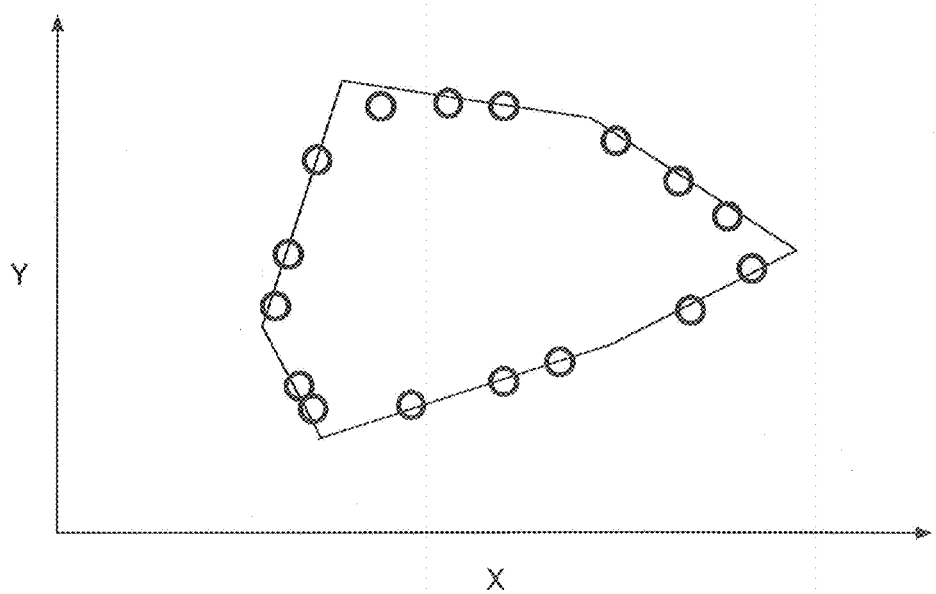
FIG. 11 is a diagram that illustrates an XY chromaticity distribution of a color member of a calibration unit and a color reproduction range of a toner image.

The calibration unit 120 is such that strip-shaped color indices 120 that are long in an X-direction are aligned on a base material in an Y-direction as illustrated in FIG. 10. As illustrated in FIG. 11, each color index 121 is composed of 16 colors that are positioned on an outer periphery of a color range (gamut) reproducible on a printed image in an XY chromaticity distribution. A spectral characteristic of the color index 121 is preliminarily measured by using a high-precision spectrometer and a matrix $R_1$ that represents a spectral characteristic of the color index 121 is preliminarily stored in the reference data storage part 117.

Here, it is preferable for the calibration unit 120 to be such that the color index 121 is provided as a replaceable one so that it is possible to change a target color intended to improve estimation precision of a spectral characteristic depending on the measurement object 10. Furthermore, a shape of the color index 121 is not limited to a strip shape but may be a different shape. Moreover, for example, the calibration unit 120 may be a recording medium, such as a paper sheet, with a plurality of different color images that are printed in a predetermined area by an image formation apparatus such as an inkjet printer or a copying machine.

As illustrated in FIG. 9, the calibration unit 120 is mounted on a stage 122 as a conveyance means and conveyed between a light irradiation position that is irradiated with light from the line illumination light source 101 and the collimator lens 102 as a light irradiation means and a waiting position that is isolated from the light irradiation position. The stage 122 conveys the calibration unit 120 from a waiting position to a light irradiation position as calibration of a transformation matrix G is executed. A case 124 that surrounds the calibration unit 120 is provided at a waiting position of the calibration unit 120. For example, the case 124 is such that internal temperature or humidity is kept to be a constant by a Peltier element, a desiccating agent, or the like. The calibration unit 120 is contained in the case 124 at a time of waiting thereof to be isolated from surrounding environment so that degradation of the color index 121 caused by influence of light, environmental temperature or humidity, or the like is suppressed.

Next, a method for calibrating a transformation matrix G in the transformation matrix calculation part 113 will be described.

As a transformation matrix G is calibrated, the calibration unit 120 together with the stage 122 are moved from a waiting position to a light irradiation position, the calibration unit 120 is irradiated with light from the line illumination light source 101, and the line sensor 107 receives light of a diffraction image to output an electric signal.

The transformation matric calculation part 113 first acquires, from the reference data storage part 117, a matrix $R_{ref}$ that represents a preliminarily measured spectral characteristic of a reference sample and a matrix $R_1$ that represent a spectral characteristic of the color index 121 of the calibration unit 120, and adds the matrix $R_1$ to the matrix $R_{ref}$ to obtain a matrix $R_{rev}$. Furthermore, a matrix $V_1$ of sensor data that are obtained from the color index 121 is added to a matrix $V_{ref}$ of sensor data that are obtained from a reference sample stored in the sensor data storage part 118, so that a matrix $V_{rev}$ is obtained.

The transformation matrix calculation part 113 obtains a transformation matrix $G_1$ by using thus obtained matrices R, and $V_{rev}$ and based on formula (6) and stores such a calibrated transformation matrix $G_1$ in the transformation matrix storage part 119. It is possible for the spectral characteristic calculation part 114 to estimate a spectral characteristic of the measurement object 10 at higher precision by using thus calibrated transformation matrix $G_1$.

Next, results of estimation of a spectral characteristic of the measurement object 10 by using a pre-calibration transformation matrix G and a calibrated transformation matrix $G_1$ in the spectral characteristic acquisition device 100 will be described. Toner images with 125 colors were used as the measurement object 10 wherein each of colors C, M, and Y is combined at an image density of any one of 1, 25, 50, 75, and 100%. Precision of estimation of a spectral characteristic was evaluated based on results of estimation of a spectral characteristic that was executed by using two transformation matrices G and $G_1$, and a color difference ($\Delta E$) from a spectral characteristic of an identical toner image that was measured by a spectrometer capable of a measurement at higher precision.

Figure 12:
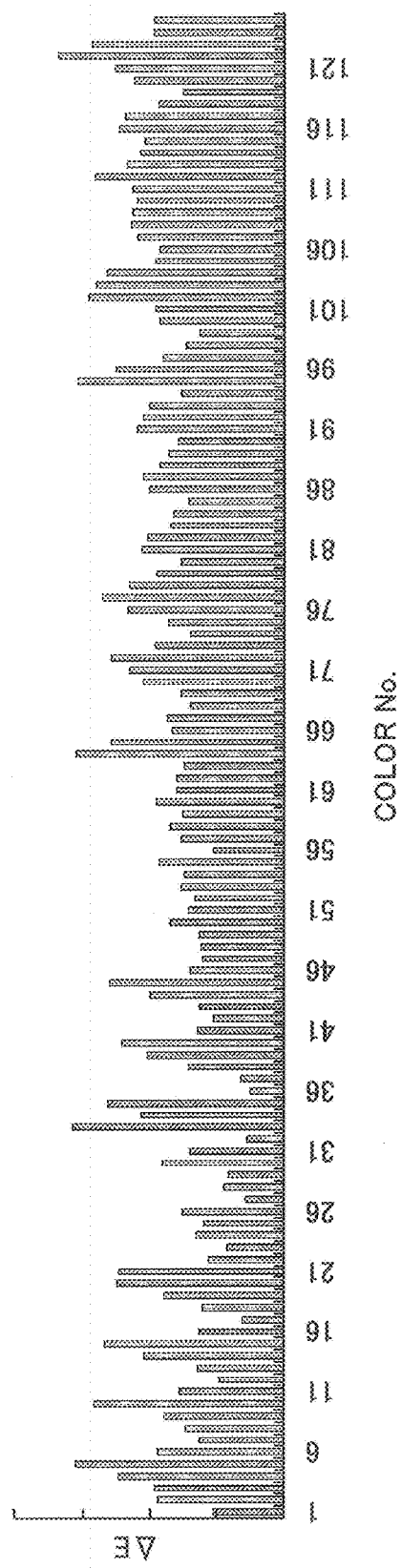
FIG. 12 is a diagram that explains estimation precision of a spectral characteristic by a spectral characteristic acquisition device.

FIG. 12 is a diagram that illustrates a spectral characteristic obtained by using a pre-calibration transformation matrix G in the spectral characteristic acquisition device 100 and a color difference ($\Delta E$) from a spectral characteristic measured by a spectrometer. Furthermore, FIG. 13 is a diagram that illustrates a spectral characteristic obtained by using a transformation matrix $G_1$ after calibration in the spectral characteristic acquisition device 100 and a color difference ($\Delta E$) from a spectral characteristic measured by a spectrometer.

Figure 13:
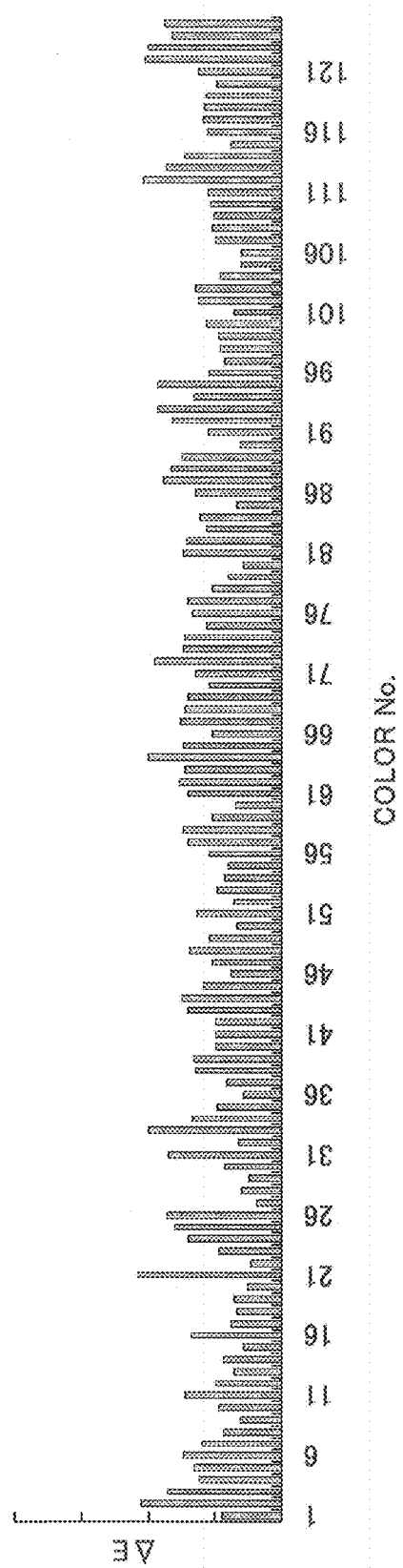
FIG. 13 is a diagram that explains estimation precision of a spectral characteristic obtained by using a calibrated transformation matrix.

As illustrated in FIG. 12 and FIG. 13, it is possible to find that a color difference ($\Delta E$) of a spectral characteristic obtained by using a calibrated transformation matrix $G_1$ (FIG. 13) was less than that of a spectral characteristic obtained by using a pre-calibration transformation matrix G (FIG. 12) so that it was possible to estimate such a spectral characteristic at a higher precision.

Thus, the spectral characteristic acquisition device 100 according to the present embodiment calibrates a transformation matrix that is used for estimation of a spectral characteristic, and thereby, it is possible to estimate a spectral characteristic of the measurement object 10 at higher precision.

Here, although 16 colors that are positioned on an outer periphery of a color range (gamut) reproducible in a printed image are used as the color indices 121 of the calibration unit 120 in the present embodiment, color indices 121 with different colors may be provided depending on a kind of or a purpose of measurement for the measurement object 10, or the like. For example, in a case where the measurement object 10 is an image of a person on a print, a color index that has a color approximating a skin color may be provided for the calibration unit 120. As a transformation matrix G is corrected by using such a color index 121, it is possible to obtain a spectral characteristic of an image of a person on a print at higher precision.

Furthermore, for example, the spectral characteristic calculation part 114 in the spectral characteristic acquisition device 100 may separately use a pre-calibration transformation matrix G and a post-calibration transformation matrix $G_1$, depending on a position of measurement of the measurement object 10. For example, in a case where a color that is had by the measurement object 10 and a color coordinate thereof are known, a spectral characteristic is calculated by using a post-calibration transformation matrix $G_1$ at a position that has a particular color whereas a spectral characteristic is calculated by using a pre-calibration transformation matrix G at other positions. Thus, transformation matrices that are used for estimation of a spectral characteristic depending on a measurement position are separately used, and thereby, it is possible to estimate, at high precision, a spectral characteristic of an area that has a particular color, without degrading precision of estimation in other areas.

Moreover, a transformation matrix G may be calibrated by using the calibration unit 120 composed of different color indices 121 so that a plurality of transformation matrices $G_2$, $G_3$, ... are obtained and stored in the transformation matrix storage part 119. It is possible to estimate a spectral characteristic by using an optimum transformation matrix depending on a position of measurement of the measurement object 10 or the like, so that precision of estimation of such a spectral characteristic is further improved.

(Correction of Sensor Data)

In the spectral characteristic acquisition device 100, a characteristic of the line illumination light source 101 may be changed by influence of a change of environment such as temperature, degradation with time, or the like, so as to change sensor data of the line sensor 107 even for an identical measurement object 10.

Herein, the correction coefficient calculation part 115 in the spectral characteristic acquisition device 100 according to the present embodiment calculates a correction coefficient for sensor data by using a reference white part provided for the calibration unit 120. The spectral characteristic calculation part 114 estimates a spectral characteristic by using sensor data multiplied by a correction coefficient obtained by the correction coefficient calculation part 115, and thereby, it is possible to estimate a spectral characteristic at high precision constantly regardless of a change of the line illumination light source 101 or the like.

The calibration unit 120 is provided with a reference white part to obtain a correction coefficient for sensor data. For example, a reference white part is a white film, a white paper sheet for printing, or the like. Here, reference sensor data $V_{wref}$ that are obtained from a reference white part is preliminarily measured and stored in the sensor data storage part 118 as a reference value.

The correction coefficient calculation part 115 acquires sensor data $v_w$ that are obtained from a reference white part of the calibration unit 120, then acquires reference sensor data $v_{wref}$ from the sensor data storage part 118, and calculates a correction coefficient w in accordance with the following formula (7):

$$Wi = v_{wref \cdot i} / v_{w \cdot i} \ (i=1, 2, \ldots, N) \quad (7)$$

In a case where a spectral characteristic of the measurement object 10 is estimated, the spectral characteristic calculation part 114 acquires sensor data v of the measurement object 10, and then, calculates corrected sensor data v' by using a correction coefficient w, in accordance with the following formula (8):

$$V' = w \cdot v \quad (8)$$

The spectral characteristic calculation part 114 produces a matrix $V_{exp}$ from sensor data v' corrected in accordance with formula (8) and estimates a spectral characteristic $R_{exp}$ of a measurement object by using a transformation matrix $G_1$ stored in the transformation matrix storage part 119 in accordance with formula (2).

Thus, the correction coefficient calculation part 115 in the spectral characteristic acquisition device 100 calculates a correction coefficient for sensor data by using a reference white part provided for the calibration unit 120. The spectral characteristic calculation part 114 calculates a spectral characteristic of the measurement object 10 by using sensor data corrected by using a correction coefficient w, and thereby, it is possible to estimate such a spectral characteristic at high precision constantly regardless of an environmental change or the like.

As described above, in accordance with the spectral characteristic acquisition device 100 according to the first embodiment, it is possible to calibrate a transformation matrix that is used for estimation of a spectral characteristic, depending on a characteristic of the measurement object 10 or the like, and it is possible to estimate a spectral characteristic of the measurement object 10 at higher precision. Furthermore, as sensor data that are outputted from the line sensor 107 are corrected, degradation of precision of estimation of a spectral characteristic that is caused by a change of the line illumination light source 101 or the like is suppressed so that it is possible to estimate a spectral characteristic at high precision constantly.

Furthermore, for example, it is possible for the spectral characteristic acquisition device 100 as illustrated in FIG. 1 and FIG. 2 to provide a high speed operation due to the line sensor 107, so that it is possible to acquire spectral characteristic of the measurement object 10 at a high speed and at once, and it is possible to be applied to a field with a required high-speed measurement, such as an inline measurement for a printed image. Moreover, it is possible for the spectral characteristic acquisition device 100 according to the present embodiment to obtain a spectral characteristic of an entire surface of the measurement object 10 and it is possible to obtain a spectral characteristic of a recording medium with an arbitrary image printed thereon or the like, as well as a color chart with a predetermined color printed at a predetermined location thereof. Therefore, it is particularly effective in a case where a color is managed strictly and a control thereof or the like is executed.

A Second Embodiment

In a second embodiment, an image evaluation device 200 will be described that includes a spectral characteristic acquisition device 100. Here, a component in a second embodiment that is identical to that of the embodiment described already will be provided with an identical numeral or letter to omit a description(s) thereof.

Figure 14:
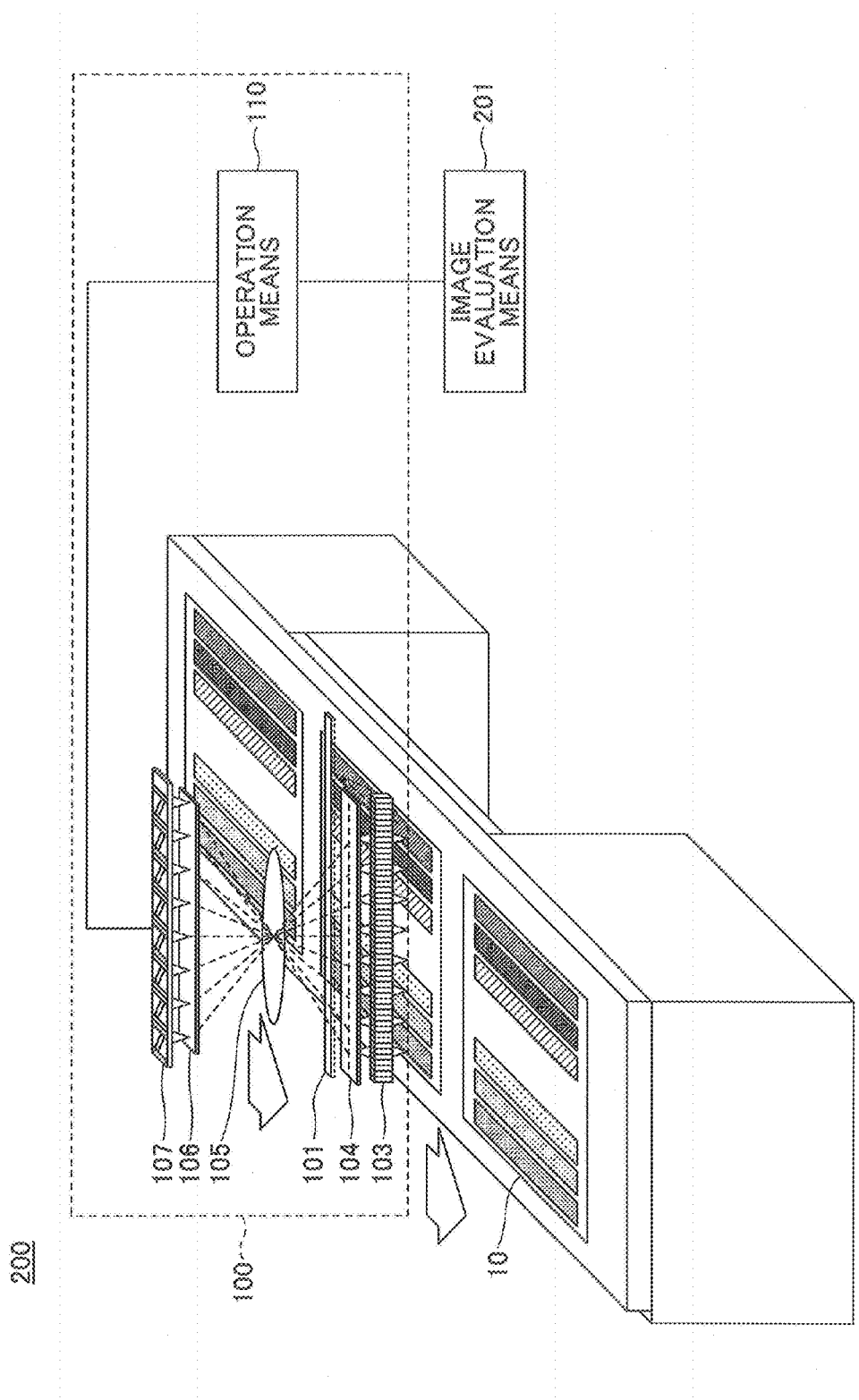
FIG. 14 is a diagram that illustrates a general configuration of an image evaluation device according to a second embodiment.

FIG. 14 is a diagram that illustrates a general configuration of an image evaluation device 200 according to a second embodiment. As illustrated in FIG. 14, the image evaluation device 200 has a spectral characteristic acquisition device 100 that includes a non-illustrated calibration unit 120, an image evaluation means 201, and a non-illustrated conveyance means that conveys a measurement object 10.

For example, the image evaluation device 200 evaluates an image formed on the measurement object 10 by an electrophotographic image formation apparatus or the like, over a full width thereof. Here, although FIG. 14 illustrates an example of the image evaluation device 200 that has one spectral characteristic acquisition device 100, for example, a plurality of spectral characteristic acquisition devices 100 may be arranged in parallel in a direction of a width of the measurement object 10.

For example, the image evaluation means 201 includes a CPU, a ROM, a main memory, and the like, wherein a program recorded in the ROM or the like is read out into the main memory and executed by the CPU and thereby each kind of function of the image evaluation means 201 is realized. However, a part or all of the image evaluation means 201 may only be realized by hardware. Alternatively, the image evaluation means 201 may physically be composed of a plurality of devices.

The conveyance means conveys the measurement object 10 in a direction of an arrow in FIG. 14. Here, although the conveyance means in the image evaluation device 200 is configured to convey the measurement object 10, the image evaluation device 200 may be configured to move relative to the measurement object 10. For a conveyance means, for example, a conveyance roller, a conveyance belt, or the like is used. It is possible for the image evaluation means 201 to calculate spectral image data over an entire surface of an image formation portion of the measurement object 10 based on information of speed that is known or provided from an encoder sensor installed in a conveyance means.

Furthermore, it is preferable for the image evaluation means 201 in the image evaluation device 200 to be capable of comparing a colorimetric result obtained by the line sensor 107 with a master image and sample and display a difference from such a master image. Thereby, it is possible for an operator to execute comparison with a master image simply. A master image may be configured in such a manner that it is possible to input a digital master image from exterior thereof, or a result of measurement of an arbitrary measurement object 10 that is measured by the image evaluation device 200 may be set as a master image.

As described above, the image evaluation device 200 according to the second embodiment is configured by using the spectral characteristic acquisition device 100, and thereby, it is possible to realize the image evaluation device 200 capable of executing, at a high speed, evaluation of a color of an image formed on a conveyed measurement object or the like. Furthermore, it is possible for the image evaluation device 200 to execute image evaluation at high precision constantly, because it is possible for the spectral characteristic acquisition device 100 to appropriately calibrate a transformation matrix that is used for estimation of a spectral characteristic and obtain such a spectral characteristic at high precision.

A Third Embodiment

In a third embodiment, an image formation apparatus 300 will be described that includes an image evaluation device 200 according to the second embodiment. Here, a component in a third embodiment that is identical to that of the embodiment described already will be provided with an identical numeral or letter to omit a description(s) thereof.

Figure 15:
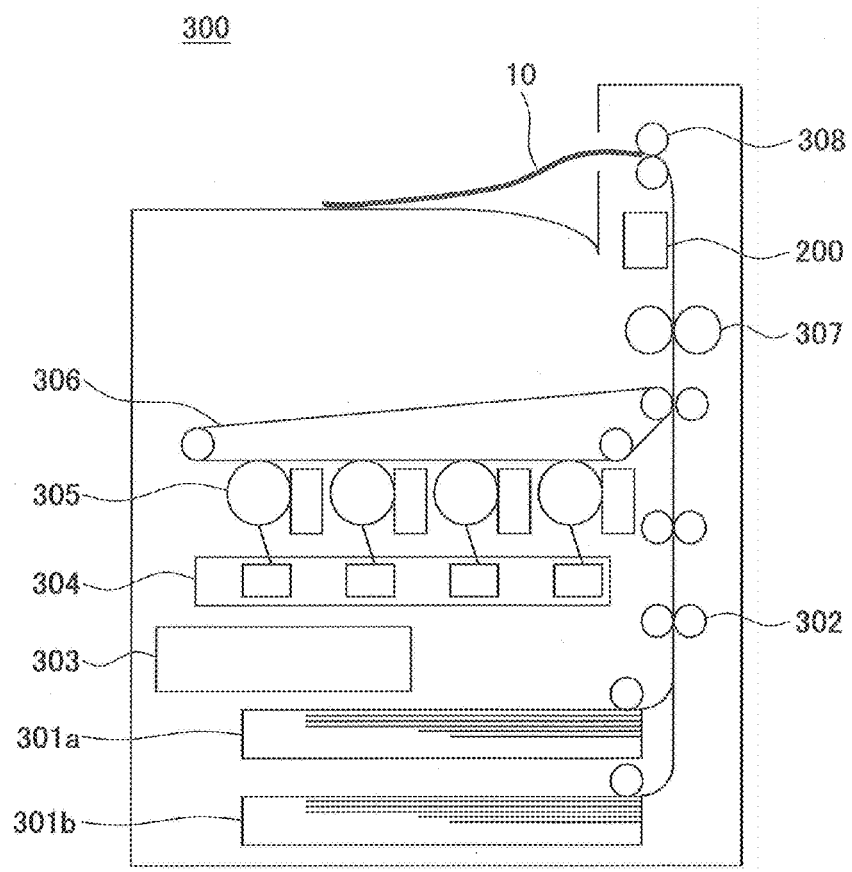
FIG. 15 is a diagram that illustrates a general configuration of an image formation apparatus according to a third embodiment.

FIG. 15 is a diagram that illustrates an image formation apparatus 300 according to a third embodiment. As illustrated in FIG. 15, the image formation apparatus 300 has an image evaluation device 200, a paper feeding cassette 301a, a paper feeding cassette 301b, a paper feeding roller 302, a controller 303, a scanning optical system 304, a photoconductor body 305, an intermediate transfer body 306, a fixing roller 307, and a paper ejection roller 308. A measurement object 10 is a recording medium such as a paper sheet.

In the image formation apparatus 300, the measurement object 10 is conveyed from the paper feeding cassette 301a or 301b and by a non-illustrated guide and the paper feeding roller 302. Simultaneously, the photoconductor body 305 is exposed to light by the scanning optical system 304 and an image provided and developed with a color material is transferred to the intermediate transfer body 306. An image transferred to the intermediate transfer body 306 is secondarily transferred to the measurement object 10 to be conveyed. An image transferred on the measurement object 10 is fixed by the fixing roller 307, and the measurement object 10 with an image formed on a surface thereof is ejected to an outside of such a machine by the paper ejection roller 308. Here, the image evaluation device 200 is placed in back of the fixing roller 307.

The image formation apparatus 300 according to the third embodiment includes the image evaluation device 200, and thereby, it is possible to acquire information of a color of an image formed on the measurement object 10 in synchronization with conveyance of the measurement object 10. Furthermore, it is possible for the image evaluation device 200 to execute image evaluation at high precision based on a spectral characteristic that is estimated by using a transformation matrix that is calibrated appropriately. Then, for example, in a case where the image formation apparatus 300 forms an image in an electrophotographic process, for example, a control means controls an output of a light source in one scanning of a writing scanning optical system or controls an image formation condition such as a pre-printing gamma correction based on an acquired result of evaluation of an image color, and thereby, it is possible to reduce an irregularity of a color of an image formed on a recording medium that is the measurement object 10.

Furthermore, for example, in a case where the image formation apparatus 300 forms an image in an inkjet process, a control means directly controls an amount of an ejected ink depending on a position of a head, and thereby, it is possible to reduce an irregularity of a color of an image formed on a recording medium.

A Fourth Embodiment

In a fourth embodiment, an image formation apparatus 400 will be described that includes an image evaluation device 200 according to the second embodiment. Here, a component in a fourth embodiment that is identical to that of the embodiment described already will be provided with an identical numeral or letter to omit a description(s) thereof.

Figure 16:
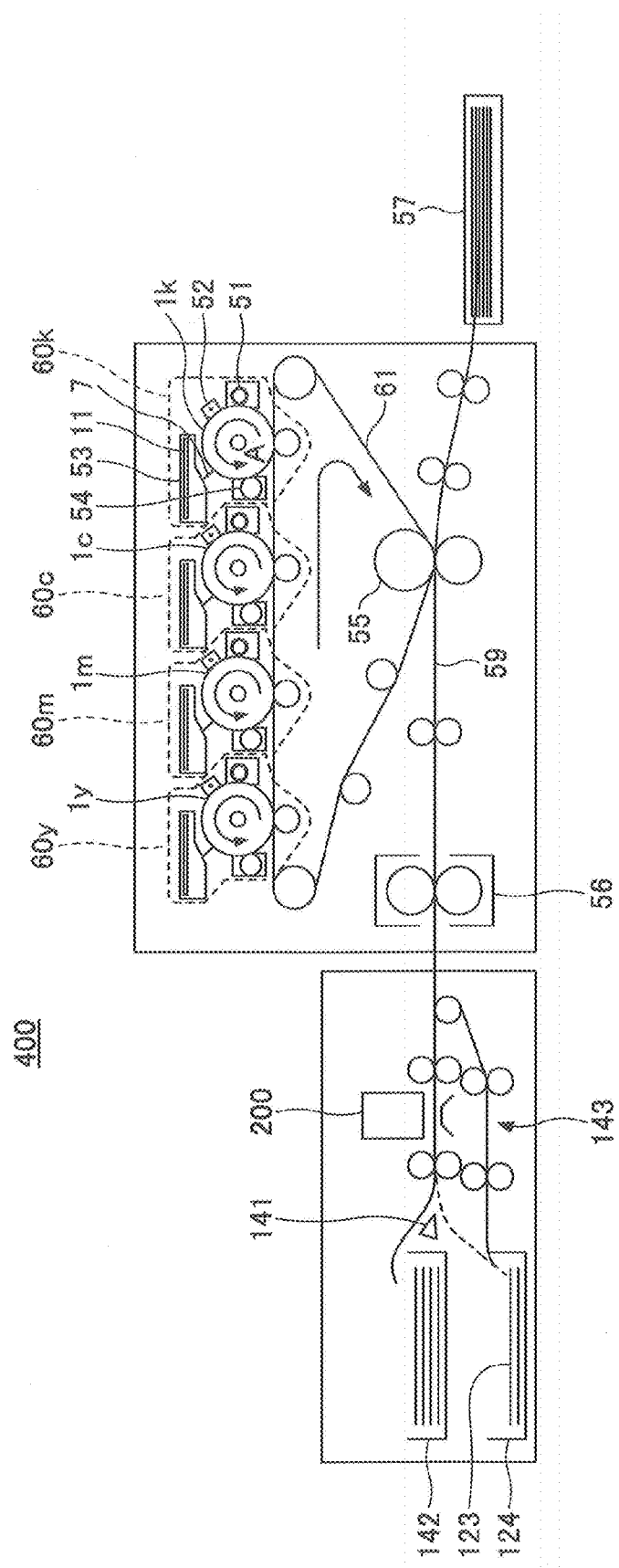
FIG. 16 is a diagram that illustrates a general configuration of an image formation apparatus according to a fourth embodiment.

FIG. 16 is a diagram that illustrates an image formation apparatus 400 according to a fourth embodiment. Among letters or numerals illustrated in FIG. 16, y, m, c, and k denote yellow, magenta, cyan, and black, respectively, wherein a letter of y, m, c, or k may be omitted for a description(s) in the following description. The image formation apparatus 400 is an electrophotographic tandem-type image formation apparatus and has a developing unit 60, an intermediate transfer belt 61, a transfer roller 55, a fixing device 56, and an image evaluation device 200. The developing unit 60 has a photoconductor drum 1, a light exposure control device 11, a cleaning device 51, an electrical charging device 52, a light exposure device 53, and a developing device 54.

In the image formation apparatus 400, the photoconductor drum 1 rotates in a direction of an arrow A in the figure and a surface of the photoconductor drum 1 is electrically charged uniformly by the electrical charging device 52. Then, the light exposure device 53 scans a surface of the photoconductor drum 1 with laser light 7 in accordance with a signal from the light exposure control device 11 so that an electrostatic latent image is formed on such a surface of the photoconductor drum 1.

An electrostatic latent image on a surface of the photoconductor drum 1 is provided with toner from the developing device 54 so as to provide a toner image. A developed toner image is transferred to the intermediate transfer belt 61. Developing units 60y, 60m, 60c, and 60k form yellow, magenta, cyan, and black toner images, respectively, and such toner images are superposed on and transferred to the intermediate transfer belt 61 so as to form a color toner image.

A color toner image formed on the intermediate transfer belt 61 is transferred, by the transfer roller 55, to a recording medium that is supplied from a paper feeding stacker 57 and conveyed on a conveyance path 59. A recording medium with a color toner image transferred thereto is conveyed to and passes through the fixing device 56, and at that time, is heated and pressed so that such a toner image is fixed on a surface thereof.

A recording medium with an image formed by an image formation process as described above is further conveyed, and is ejected onto a paper ejection stacker 142 after color information of such an image is acquired by the image evaluation device 200. In the image formation apparatus 400, an image formation condition is controlled based on a result of image evaluation of the image evaluation device 200, and thereby, it is possible to keep a quality of an image formed on a recording medium to be constant.

The image formation apparatus 400 according to the present embodiment has a color index sample 123, a case 124 that stores the color index sample 123, a conveyance means 143 that conveys the color index sample 123, and a paper ejection bifurcation device 141.

For example, the color index sample 123 is one example of a calibration color index, and is a recording medium, such as a paper sheet, with a color index image printed on a surface thereof. The conveyance means 143 is configured to include a plurality of conveyance roller pairs or the like and conveys the color index sample 123. The image evaluation device 200 uses sensor data obtained from the color index sample 123 conveyed by the conveyance means 143 so as to calibrate a transformation matrix. Here, the image formation apparatus 400 may have a plurality of color index samples 123 that have different color index images.

The conveyance means 143 again conveys, to the case 124, the color index sample 123 conveyed from the case 124 and used for calibration of a transformation matrix in the image evaluation device 200. The paper ejection bifurcation device 141 ejects, onto the paper ejection stacker 142, a recording medium provided with an image formed by the developing unit 60 or the like and having passed through the fixing device 56, wherein an angle of a bifurcating claw is controlled in such a manner that the color index sample 123 used for calibration of a transformation matric in the image evaluation device 200 returns to the case 124.

The color index sample 123 is conveyed to be interposed between a recording medium and a recording medium in such a manner that calibration of a transformation matrix in the image evaluation device 200 is executed at arbitrary timing. For example, calibration of a transformation matrix is executed in a case where the number of continuously measured recording media reaches 50, a case where a result of detection of a temperature sensor is changed by ±5° C. with respect to a reference value, or the like. Furthermore, for example, execution thereof is caused in a case where a total number of measured ones reaches a constant value, a case where a monitored electric current value of a light source reaches a set amount of a change thereof, a case where maintenance or conveyance of the image formation apparatus 400 is executed, a case where a measurement is stopped urgently, a case where a light source is replaced, or the like.

According to the fourth embodiment, it is possible for the image evaluation device 200 to execute image evaluation at high precision based on a spectral characteristic that is estimated by using a transformation matrix that is calibrated appropriately. Therefore, the image formation apparatus 400 adjusts an image formation condition or the like based on a result of image evaluation in the image evaluation device 200, and thereby, it is possible to stably output an image at a high quality wherein color irregularity or the like is not caused even with time.

A Fifth Embodiment

Next, a fifth embodiment will be described. Here, a component in a fourth embodiment that is identical to that of the embodiment described already will be provided with an identical numeral or letter to omit a description(s) thereof.

Figure 17:
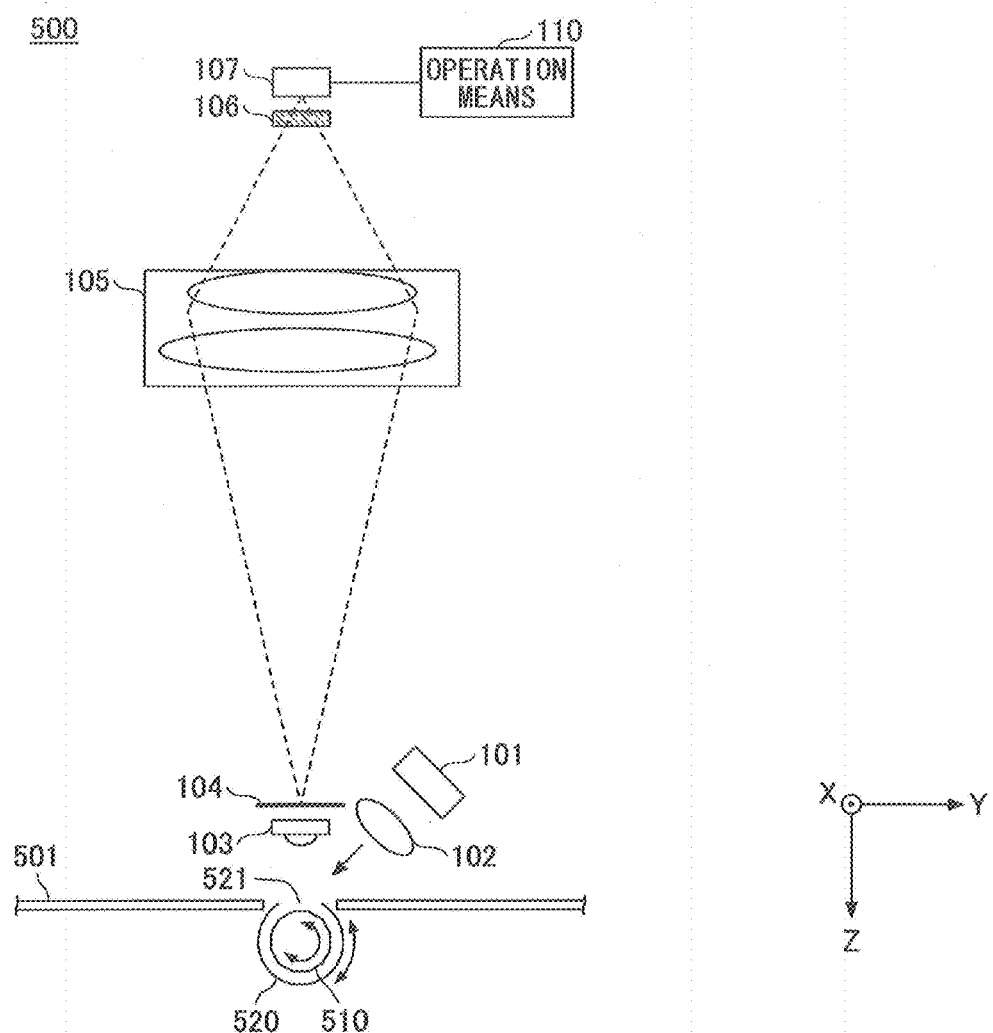
FIG. 17 is a diagram that illustrates a general configuration of a spectral characteristic acquisition device according to a fifth embodiment.

FIG. 17 is a side view that illustrates a general configuration of a spectral characteristic acquisition device 500 according to a fifth embodiment.

The spectral characteristic acquisition device 500 is provided with a calibration unit 510 as a calibration color index and a cover member 520 with a circularly hollow or cylindrical shape that covers the calibration unit 510 at a lower side of a supporting plate 501 that supports a measurement object 10 to be conveyed or mounted thereon (an opposite side of a line illumination light source 101). The supporting plate 501 is provided with an aperture in such a manner that it is possible to expose at least a portion of the calibration unit 510 to the line illumination light source 101 or the like.

Figure 18:
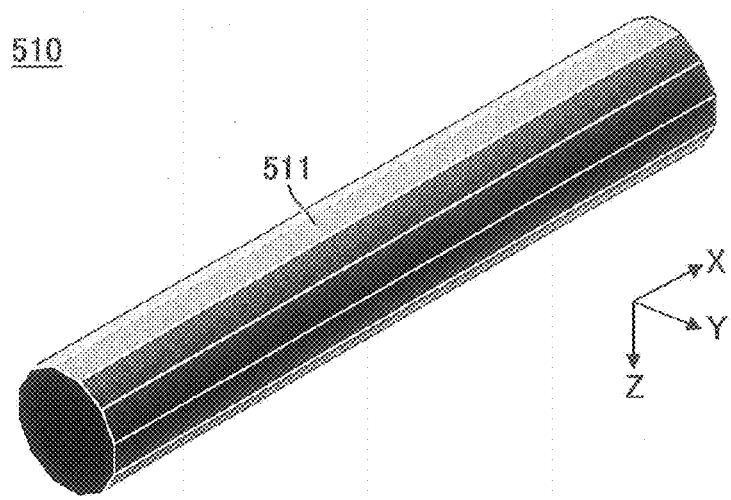
FIG. 18 is a diagram that illustrates a calibration unit in a fifth embodiment.

FIG. 18 is a diagram that illustrates a calibration unit 510 in the fifth embodiment. For example, the calibration unit 510 is composed of a columnar member that is formed by applying a cutting operation to a metallic material such as aluminum, and a plurality of color indices 511 provided on an outer peripheral surface of such a columnar member. For example, A color index 511 has a strip-like shape and is bonded to a planar portion at an outer periphery of a columnar member by a double-faced tape or the like. Furthermore, the calibration unit 510 is provided with a reference white part on an outer peripheral surface thereof, so that it is possible to correct sensor data by using such a reference white part.

Furthermore, for example, the calibration unit 510 is connected to a driving means, such as a motor, that is not illustrated in FIG. 17, via a decelerating mechanism composed of a plurality of gears or the like, and provided rotatably in one direction or both directions centered at a rotation axis parallel to an X-direction.

Here, the calibration unit 510 according to the fifth embodiment has a polygonal shape but may be of a different shape such as a circularly columnar shape.

Figure 19:
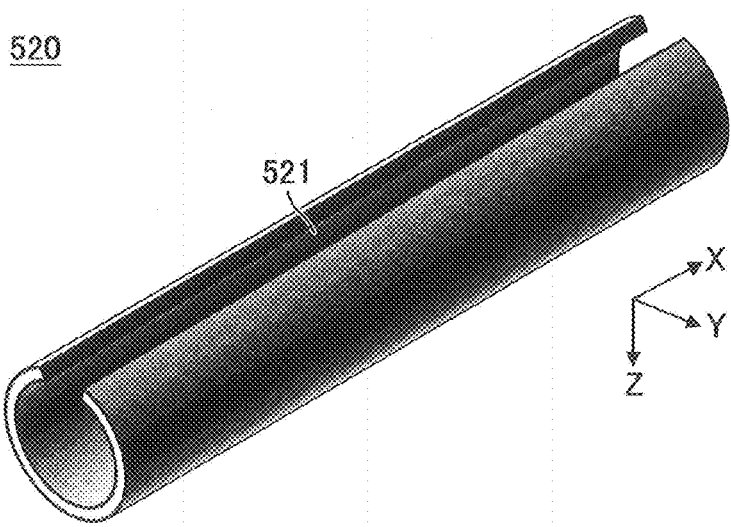
FIG. 19 is a diagram that illustrates a cover member in a fifth embodiment.

FIG. 19 is a diagram that illustrates a cover member 520 in the fifth embodiment.

For example, the cover member 520 is formed into a hollow or cylindrical shape by applying a cutting process, a pressing process, or the like to a metallic material such as aluminum, and a portion at an outer periphery thereof is provided with an aperture 521. For example, a surface of the cover member 520 is blackened by an alumite process, coating, or the like, in order to suppress a measurement error caused by light reflection or the like.

Furthermore, for example, the cover member 520 is connected to a driving means such as a motor that is not illustrated in FIG. 17 via a decelerating mechanism composed of a plurality of gears or the like, and provided rotatably in one direction or both directions centered at a rotation axis parallel to an X-direction.

As illustrated in FIG. 17, for example, the cover member 520 is provided in such a manner that the calibration unit 510 is contained in an interior thereof and thereby paper powder, dust, or the like, that is produced from a measurement object 10 such an a paper sheet is prevented from attaching to the calibration unit 510.

For example, in a case where calibration of a transformation matrix or calculation of a sensor data correction coefficient are executed similarly to the first embodiment, the cover member 520 rotates in such a manner that the color index 511 of the calibration unit 510 is exposed to the line illumination light source 101 through the aperture 521 as illustrated in FIG. 17.

Calibration of a transformation matrix is executed based on sensor data of the plurality of color indices 511 that are acquired by rotating the calibration unit 510, or the like. Furthermore, calculation of a sensor data correction coefficient is executed based on senor data of a reference white part that are acquired by rotating the calibration unit 510 so as to expose such a reference white part, or the like. Here, the calibration unit 510 is rotated to acquire sensor data of the color indices 511 and such a reference white part, and thereby, it is also possible to execute calculation of senor data correction coefficient simultaneously with calibration of a transformation matrix.

Figure 20:
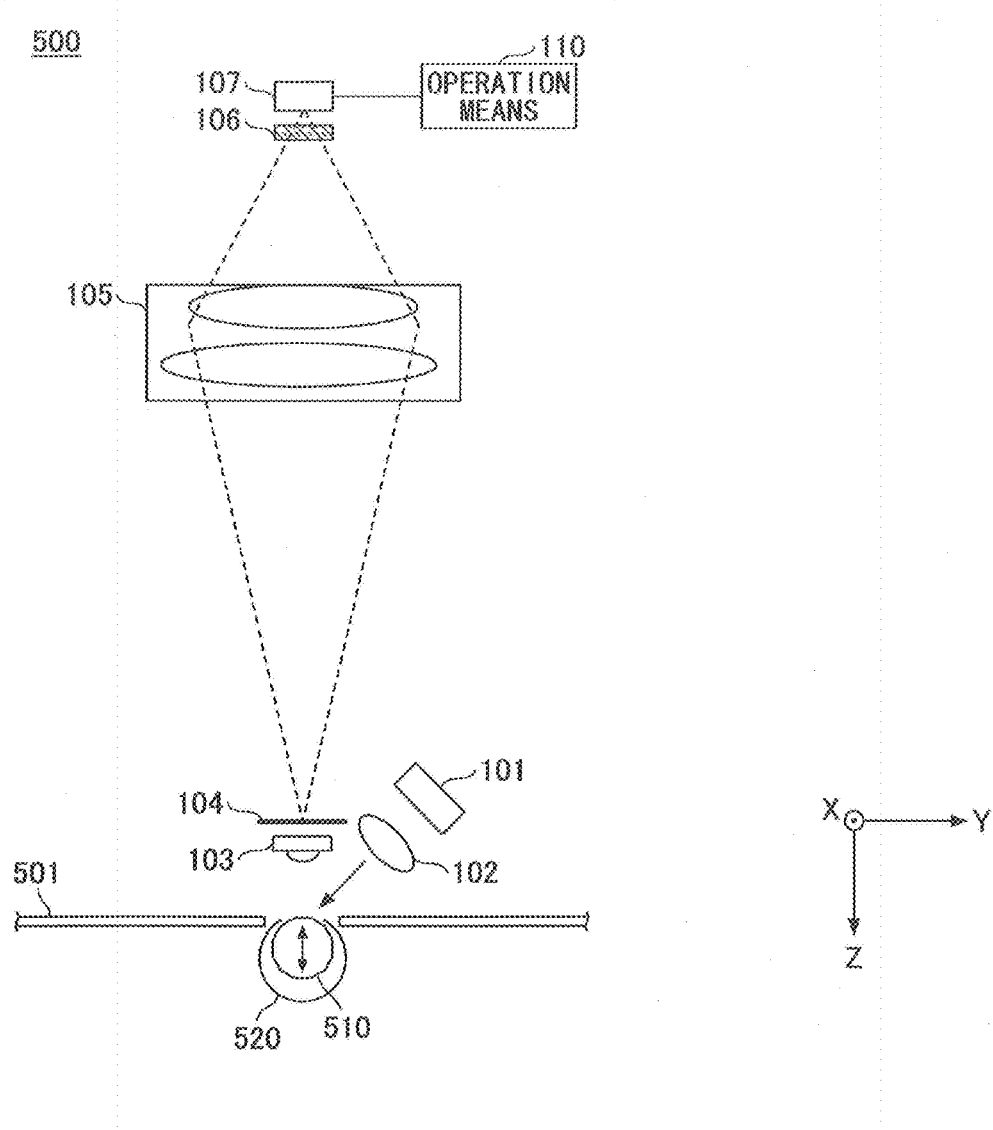
FIG. 20 is a diagram that illustrates an operation of a calibration unit in a fifth embodiment.

Herein, as illustrated in FIG. 20, the calibration unit 510 may be provided accessibly or detachably with respect to a light irradiation position for the line illumination light source 10 so as to move between a containment position for the cover member 520 and a spectral characteristic measurement position. In such a configuration, it is possible to execute calibration of a transformation matrix or calculation of sensor data correction coefficient from a result of measurement on a condition identical to that in a case where a spectral characteristic of the measurement object 10 is measured, and it is possible to reduce an influence of a light irradiation angle difference or a defocus and execute calibration of a transformation matrix or the like at higher precision.

Figure 21:
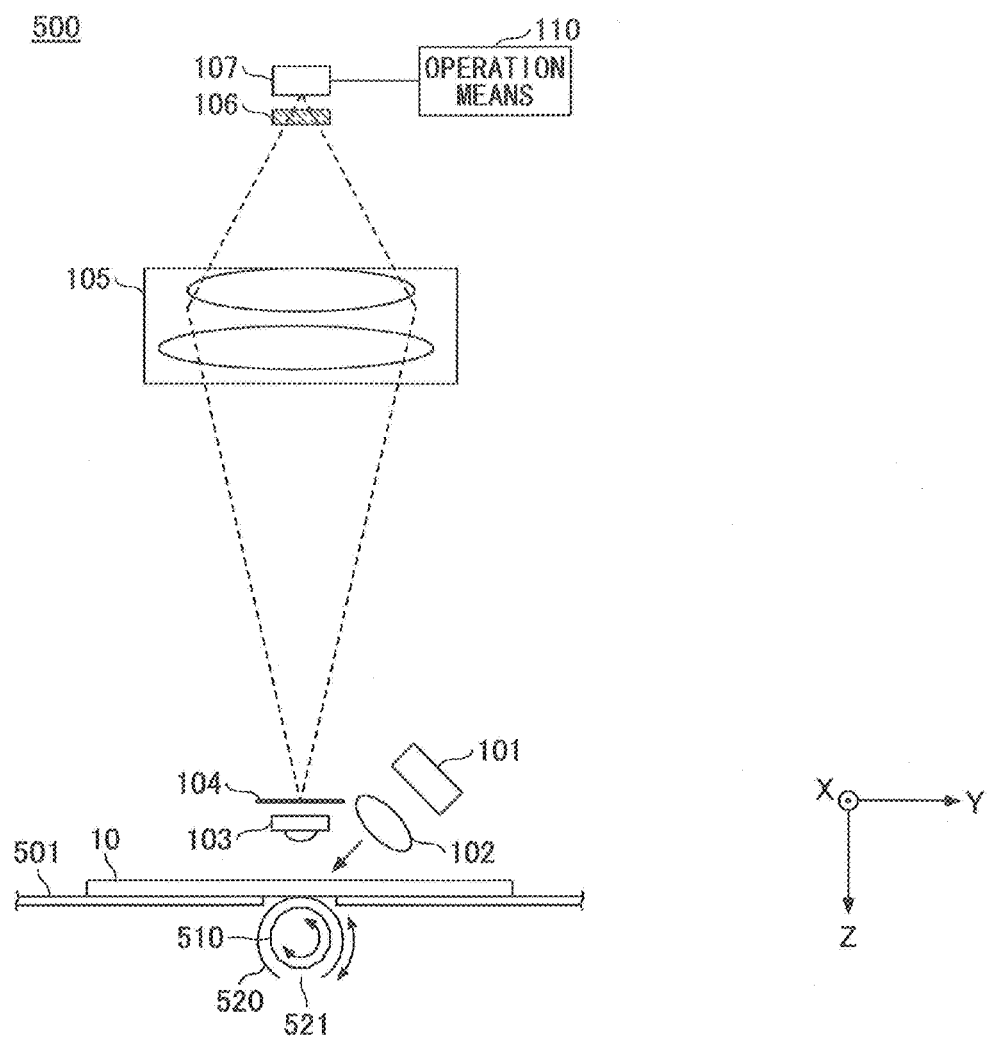
FIG. 21 is a diagram that illustrates an operation of a cover member in a fifth embodiment.

Furthermore, in a case where a spectral characteristic of the measurement object 10 is measured, the cover member 520 rotates in such a manner that the aperture 521 is positioned at a lower side thereof, and the calibration unit 510 is covered by the cover member 520 to be shielded from the line illumination light source 10, as illustrated in FIG. 21.

Herein, it is preferable for the cover member 520 to be provided in such a manner that a top portion of an outer peripheral surface and a position of the measurement object 10 supported by the supporting plate 501 are positioned at an identical height in a Z-direction on a condition that the calibration unit 510 is covered. Due to such a configuration, deformation of the measurement object 10 mounted on the supporting plate 501, upward and downward flopping of the measurement object 10 conveyed on the supporting plate 501, or the like, is suppressed, and thereby, it is possible to obtain a spectral characteristic of the measurement object 10 at high precision.

Figure 22:
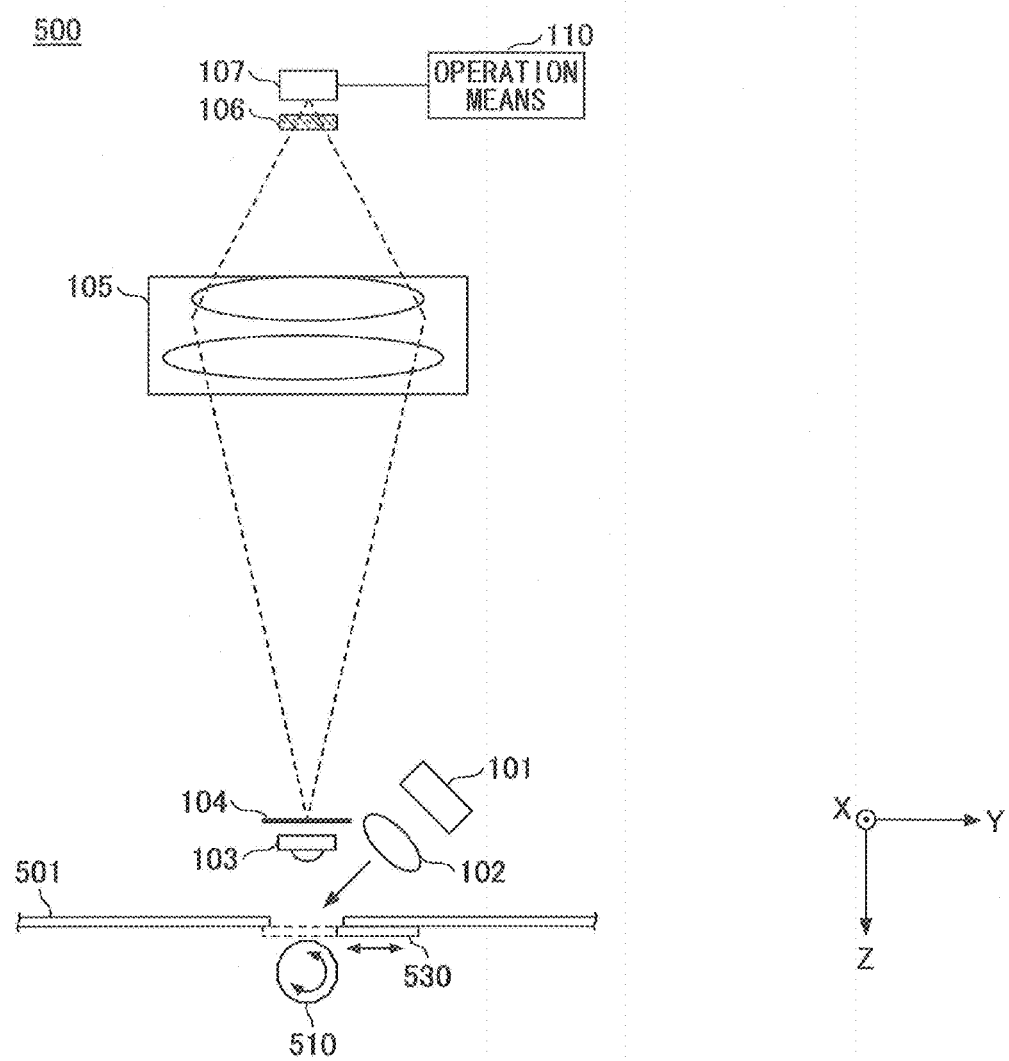
FIG. 22 is a side view that illustrates a general configuration of a spectral characteristic acquisition device according to a fifth embodiment.

Here, a cover member is not limited to a hollow or cylindrical shape as described above, and may be, for example, a flat-plate-shaped shutter 530 that opens or closes an aperture of the supporting plate 501, as illustrated in FIG. 22. For example, the shutter 530 is operated so as to open at a time of calibration of a transformation matrix, calculation of a correction coefficient, or the like, or close at a time of measurement of the measurement object 10 or non-operation of the spectral characteristic acquisition device 500, and thereby, attachment of paper powder, dust, or the like to the calibration unit 510 is prevented.

As described above, for example, the calibration unit 510 is covered by the cover member 520 that is provided movably, at a time of measurement of a spectral characteristic, non-operation of the spectral characteristic acquisition device 500, or the like, according to the fifth embodiment, and thereby, for example, attachment of paper powder, dust, or the like to the calibration unit 510 is prevented. Therefore, it is possible to execute calibration of a transformation matrix, calculation of a sensor data correction coefficient, or the like, at high precision constantly, and obtain a spectral characteristic of the measurement object 10 at high precision for a long period of time.

Here, the spectral characteristic acquisition device 500 may be mounted on an image evaluation device 200 according to the second embodiment. It is possible for the image evaluation device 200 with the spectral characteristic acquisition device 500 mounted thereon to execute calibration of a transformation matrix or calculation of a sensor data correction coefficient during the measurement object 10 is conveyed, and thereby, it is possible to obtain a spectral characteristic at higher precision. Furthermore, the image evaluation device 200 with the spectral characteristic acquisition device 500 mounted thereon may be installed in an image formation apparatus 300 or 400.

A Sixth Embodiment

Next, a sixth embodiment will be described. Here, a component in a sixth embodiment that is identical to that of the embodiment described already will be provided with an identical numeral or letter to omit a description(s) thereof.

Figure 23:
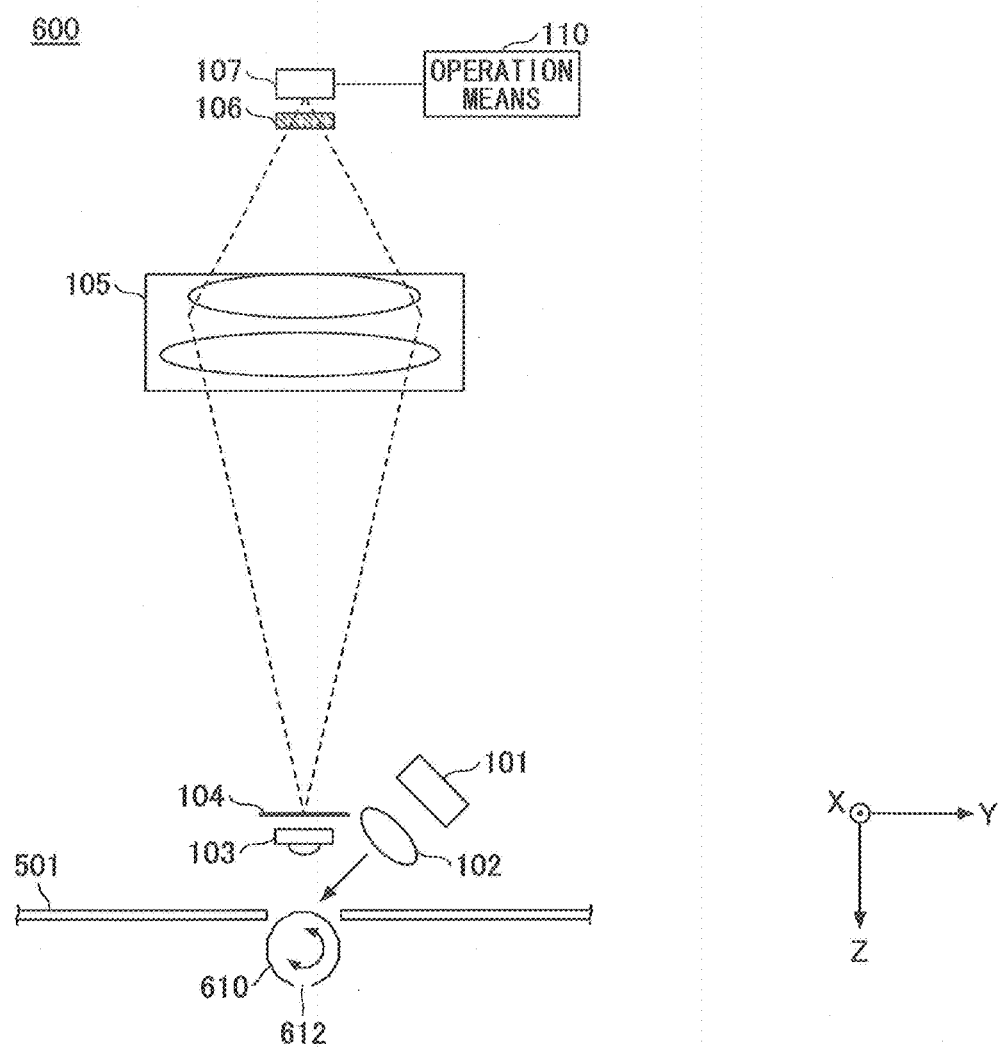
FIG. 23 is a side view that illustrates a general configuration of a spectral characteristic acquisition device according to a sixth embodiment.

FIG. 23 is a side view that illustrates a general configuration of a spectral characteristic acquisition device 600 according to a sixth embodiment.

The spectral characteristic acquisition device 600 is such that a calibration unit 610 as a calibration color index is provided at a lower side of a supporting plate 501 that supports a measurement object 10 to be conveyed or mounted thereon (an opposite side of a line illumination light source 101).

Figure 24:
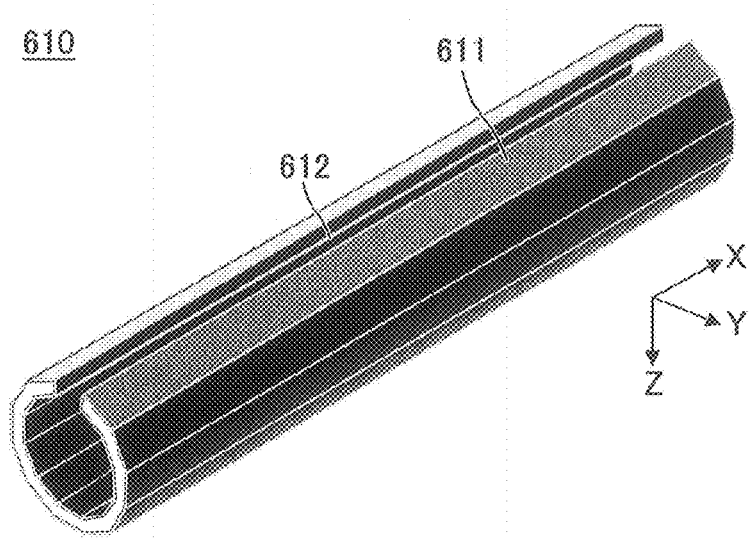
FIG. 24 is a diagram that illustrates a calibration unit in a sixth embodiment.

FIG. 24 is a diagram that illustrates a calibration unit 610 in the sixth embodiment.

For example, the calibration unit 610 is composed of a hollow or cylindrical member that is formed by applying a cutting process, a pressing process, or the like, to a metallic material such as aluminum and has an aperture 612 at a part thereof, and a plurality of color indices 611 provided on an outer peripheral surface of such a hollow or cylindrical member. For example, a color index 611 has a strip-like shape and is bonded to a planar portion at an outer periphery of such a hollow or cylindrical member by a double-faced tape or the like. Furthermore, the calibration unit 610 is provided with a reference white part on an outer peripheral surface thereof, and thereby, it is possible to correct sensor data by using such a reference white part. For example, an inner peripheral surface of the calibration unit 610 is blackened by an alumite process, coating, or the like, so as to absorb light incident thereon.

Furthermore, for example, the calibration unit 610 is connected to a driving means such as a motor that is not illustrated in FIG. 23 via a decelerating mechanism calibrated by a plurality of gears or the like, and provided rotatably in one direction or both directions centered at a rotation axis parallel to an X-direction.

Here, the calibration unit 610 according to the sixth embodiment has a polygonal hollow or cylindrical shape but may have a different shape such as a circularly cylindrical shape.

In the spectral characteristic acquisition device 600, the calibration unit 610 rotates in such a manner that the color indices 611 or a reference white part is irradiated with light, and thereby, calibration of a transformation matrix or calculation of a sensor data correction coefficient is executed based on sensor data obtained from the color indices 611 or such a reference white part.

Herein, for example, dark electric current of a line sensor 107 may be increased by a change in environmental temperature or the like in the spectral characteristic acquisition device 600 so as to cause a dispersion of a measurement result. Dark electric current is electric current flowing on a condition that no pixel of the liner senor 107 is irradiated with light, and for example, dark electric current is approximately doubled as temperature raises by 7-10° C.

Herein, a correction coefficient calculation part 115 in the spectral characteristic acquisition device 600 according to sixth embodiment calculates a correction coefficient that corrects output data from the line sensor 107 so as to eliminate an influence of dark electric current. A spectral characteristic calculation part 114 estimates a spectral characteristic by using sensor data multiplied by a correction coefficient obtained by the correction coefficient calculation part 115, and thereby, it is possible to obtain a spectral characteristic at high precision constantly, independently of an increase or decrease in dark electric current or the like.

Figure 25:
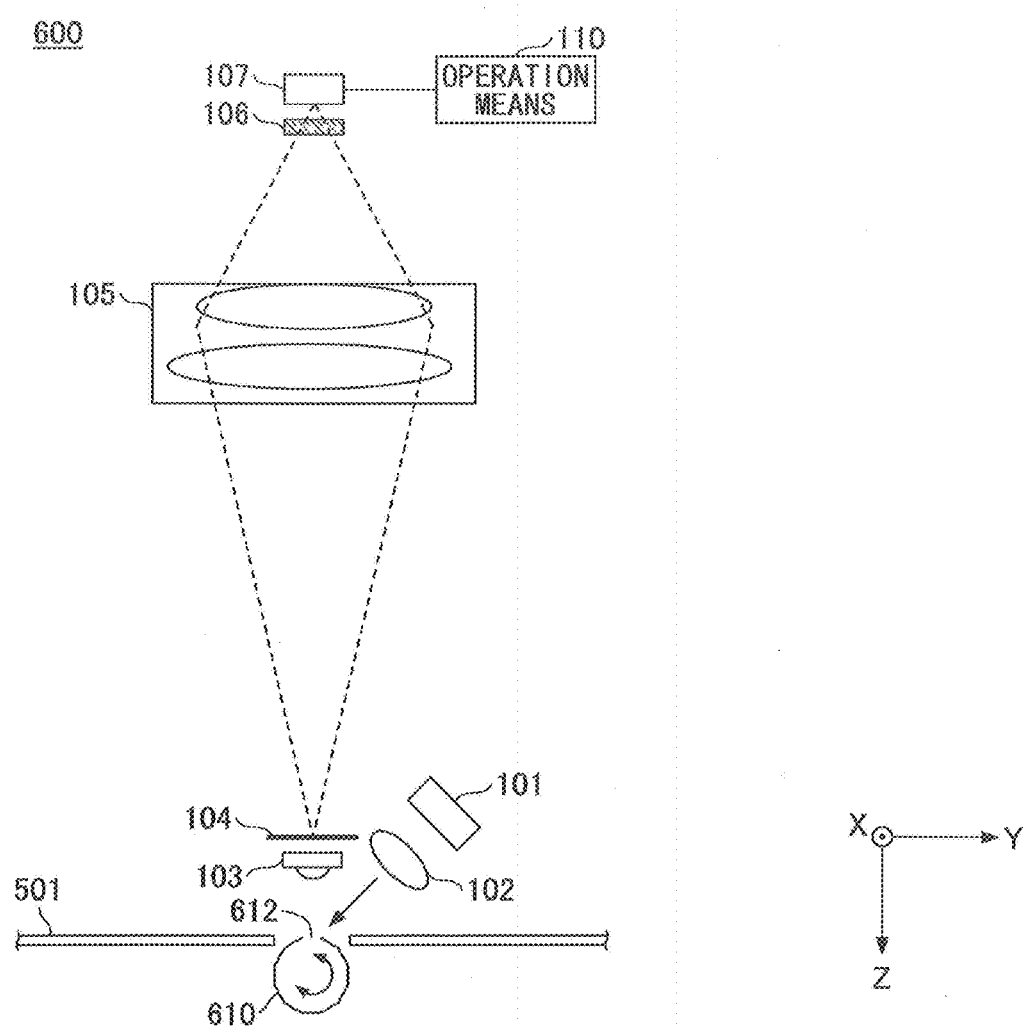
FIG. 25 is a diagram that illustrates an operation of a calibration unit in a sixth embodiment.

In a case where a correction coefficient is calculated, the calibration unit 610 rotates in such a manner that light irradiating from a line illumination light source 101 is incident on the aperture 612 as illustrated in FIG. 25. Light incident on the aperture 612 of the calibration unit 610 is absorbed by an interior of the calibration unit 610 so that no reflected light reaches the line sensor 107.

The correction coefficient calculation part 115 acquires sensor data $v_d$ from the line sensor 107 on a condition that the aperture 612 of the calibration unit 610 is irradiated with light. Furthermore, the correction coefficient calculation part 115 acquires sensor data $v_w$ from the line sensor 107 on a condition that the calibration unit 610 rotates in such a manner that a reference white part is irradiated with light from the line illumination light source 101.

Reference sensor data $V_{wref}$ obtained from a reference white part of the calibration unit 610 and reference sensor data $V_{dref}$ obtained from the aperture 612 of the calibration unit 610 at a time of measurement of $V_{wref}$ are stored in a sensor data storage part 118 as reference values.

As the correction coefficient calculation part 115 acquires sensor data $v_d$ and $v_w$, reference sensor data $V_{wref}$ and $V_{dref}$ are acquired from the sensor data storage part 118 and a correction coefficient w is calculated in accordance with the following formula (9):

$$w_i = (v_{wref\text{-}i} - v_{dref\text{-}i})/(v_{w\text{-}i} - v_{d\text{-}i}) \ (i=1, 2, \ldots N) \quad (9)$$

As the spectral characteristic calculation part 114 acquires sensor data v of the measurement object 10 in a case where a spectral characteristic of the measurement object 10 is estimated, a correction sensor data v' is calculated in accordance with the following formula (10):

$$v_i' = w \cdot (v_i - v_{d\text{-}i}) \ (i=1, 2, \ldots N) \quad (10)$$

by using a correction coefficient w obtained in accordance with formula (9) described above.

The spectral characteristic calculation part 114 produces a matrix $V_{exp}$ from sensor data v' corrected in accordance with formula (10) and estimates a spectral characteristic $R_{exp}$ of a measurement object in accordance with formula (2) by using a transformation matrix $G_1$ stored in the transformation matrix storage part 119.

Thus, a correction coefficient is calculated based on sensor data acquired from a reference white part and an aperture of the calibration unit 610 and sensor data acquired from the measurement object 10 are corrected thereby, so that it is possible to reduce a dispersion of an output from the line sensor 107 that is caused by an increase of decrease in dark electric current. Therefore, according to the sixth embodiment, it is possible to reduce a dispersion of an output from the line sensor 107 and thereby obtain a spectral characteristic of the measurement object 10 at higher precision for a long period of time.

Here, for example, a cover member that covers a periphery of the calibration unit 610 or a flat-plate-shaped shutter that opens or closes an aperture of a supporting plate 501 may be provided. For example, such a cover member or a shutter is provided, and thereby, it is possible to prevent paper powder, dust, or the like, that is produced from the measurement object 10 such as a paper sheet, from attaching to the calibration unit 610.

Furthermore, the spectral characteristic acquisition device 600 may be mounted in the image evaluation device 200 according to the second embodiment. It is possible for the image evaluation device 200 with the spectral characteristic acquisition device 600 mounted thereon to execute calibration of a transformation matrix or calculation of sensor data correction coefficient during the measurement object 10 is conveyed, and it is possible to obtain a spectral characteristic at higher precision. Furthermore, the image evaluation device 200 with the spectral characteristic acquisition device 600 mounted thereon may be installed in an image formation apparatus 300 or 400.

The spectral characteristic acquisition device 100, 500, or 600 is not limited to an embodiment as described above and is capable of being installed in a variety of devices or apparatuses other than an image evaluation device and an image formation apparatus. For example, the spectral characteristic acquisition device 100, 500, or 600 may be provided on a check device that checks reliability of a paper money, a credit card, or the like.

Although a spectral characteristic acquisition device, an image evaluation device, and an image formation apparatus according to embodiments have been described above, an embodiment of the present invention is not limited to the embodiments described above and a variety of alterations and modifications are possible within a scope of the present invention.

APPENDIX

<An Illustrative Embodiment(s) of a Spectral Characteristic Acquisition Device, an Image Evaluation Device, and an Image Formation Apparatus>

At least one illustrative embodiment of the present invention may relate to at least one of a spectral characteristic acquisition device, an image evaluation device, and an image formation apparatus.

At least one illustrative embodiment of the present invention may be provided while a description(s) provided above is/are taken into consideration, and may aim at providing a spectral characteristic acquisition device capable of calibrating a transformation matrix appropriately and estimating a spectral characteristic at high precision.

According to at least one illustrative embodiment of the present invention, there may be provided a spectral characteristic acquisition device that has a light irradiation means that irradiates an object with light, a diffraction means that diffracts light reflected from the object to form a diffraction image, a light-receiving means that receives the diffraction image and outputs a signal depending on an amount of light in each different wavelength band, a spectral characteristic calculation means that estimates a spectral characteristic by using a preset transformation matrix and based on a signal output from the light-receiving means that is obtained from the object, a calibration color index that has a color with a known spectral characteristic, and a transformation matrix calibration means that calibrates the transformation matrix by using a signal output from the light-receiving means that is obtained from the calibration color index.

Illustrative Embodiment (1) is a spectral characteristic acquisition device, characterized by having a light irradiation means that irradiates an object with light, a diffraction means that diffracts light reflected from the object to form a diffraction image, a light-receiving means that receives the diffraction image and outputs a signal depending on an amount of light in each different wavelength band, a spectral characteristic calculation means that estimates a spectral characteristic by using a preset transformation matrix and based on a signal output from the light-receiving means that is obtained from the object, a calibration color index that has a color with a known spectral characteristic, and a transformation matrix calibration means that calibrates the transformation matrix by using a signal output from the light-receiving means that is obtained from the calibration color index.

Illustrative Embodiment (2) is the spectral characteristic acquisition device as described in Illustrative Embodiment (1), characterized in that the calibration color index has a reference white part, and by having a correction coefficient calculation means that calculates a correction coefficient for correcting a signal output from the light-receiving means that is obtained from the object based on a signal output from the light-receiving means that is obtained from the reference white part and a preset reference value.

Illustrative Embodiment (3) is the spectral characteristic acquisition device as described in Illustrative Embodiment (1) or (2), characterized by having a conveyance means that conveys the calibration color index between a light irradiation position that is irradiated with light from the light irradiation means and a waiting position that is isolated from the light irradiation position.

Illustrative Embodiment (4) is the spectral characteristic acquisition device as described in Illustrative Embodiment (3), characterized by having a case that surrounds the calibration color index at the waiting position.

Illustrative Embodiment (5) is the spectral characteristic acquisition device as described in Illustrative Embodiment (1) or (2), characterized in that the calibration color index has a columnar shape and is provided rotatably at a light irradiation position that is irradiated with light from the light irradiation means.

Illustrative Embodiment (6) is the spectral characteristic acquisition device as described in Illustrative Embodiment (5), characterized in that the calibration color index is provided accessibly or detachably to the light irradiation position.

Illustrative Embodiment (7) is the spectral characteristic acquisition device as described in Illustrative Embodiment (5) or (6), characterized by having a cover member that is provided movably in such a manner that the calibration color index is exposed to or shielded from the light irradiation means.

Illustrative Embodiment (8) is the spectral characteristic acquisition device as described in Illustrative Embodiment (1), characterized in that the calibration color index has a reference white part and a hollow or cylindrical shape provided with an aperture and is provided rotatably at a light irradiation position that is irradiated with light from the light irradiation means, and by having a correction coefficient calculation means that calculates a correction coefficient for correcting a signal output from the light-receiving means that is obtained from the object, based on a signal output from the light-receiving means that is acquired from each of the reference white part and the aperture of the calibration color index and a preset reference value.

Illustrative Embodiment (9) is an image evaluation device, characterized by having the spectral characteristic acquisition device as described in any one of Illustrative Embodiments (1) to (8), and an image evaluation means that evaluates an image formed on the object based on a spectral characteristic obtained by the spectral characteristic acquisition device.

Illustrative Embodiment (10) is an image formation apparatus, characterized by having the image evaluation device as described in Illustrative Embodiment (9).

According to at least one illustrative embodiment of the present invention, it may be possible to provide a spectral characteristic acquisition device capable of calibrating a transformation matrix appropriately and estimating a spectral characteristic at high precision.

Although the illustrative embodiment(s) and specific example(s) of the present invention have been described with reference to the accompanying drawing(s), the present invention is not limited to any of the illustrative embodiment(s) and specific example(s), and the illustrative embodiment(s) and specific example(s) may be altered, modified, or combined without departing from the scope of the present invention.

The present application is based on and claims the benefit of priority to Japanese Patent Application No. 2014-030270 filed on Feb. 20, 2014, Japanese Patent Application No. 2014-099572 filed on May 13, 2014, and Japanese Patent Application No. 2014-255400 filed on Dec. 17, 2014, the entire contents of which are herein incorporated by reference.

What is claimed is:

1. A spectral characteristic acquisition device, comprising:
    a light irradiation part configured to irradiate an object with light;
    a diffraction part configured to diffract light reflected from the object to provide diffracted light;
    a light-receiving part configured to receive the diffracted light and output a signal based on an amount of the diffracted light;
    a calibration color index configured to include a color with a known spectral characteristic; and
    an operation part configured to calculate a spectral characteristic of the object from a signal output from the light-receiving part by using a predetermined transformation matrix and calibrate the transformation matrix by using the calibration color index.

2. The spectral characteristic acquisition device as claimed in claim 1, wherein the calibration color index is further configured to include a reference white part and the operation part is further configured to correct a signal output from the light-receiving part by using the reference white part.

3. The spectral characteristic acquisition device as claimed in claim 1, further comprising:
    a movement part configured to move the calibration color index.

4. The spectral characteristic acquisition device as claimed in claim 3, further comprising:
    a case configured to surround the calibration color index.

5. The spectral characteristic acquisition device as claimed in claim 1, wherein the calibration color index is configured to include a columnar surface and be rotatable.

6. The spectral characteristic acquisition device as claimed in claim 5, further comprising:
    a movement part configured to move the calibration color index.

7. The spectral characteristic acquisition device as claimed in claim 5, further comprising:
   a cover member configured to cover a portion of the columnar surface.

8. The spectral characteristic acquisition device as claimed in claim 2, wherein the calibration color index is further configured to include a cylindrical surface with an aperture and be rotatable, and the operation part is further configured to correct a signal output from the light-receiving part by using the aperture.

9. An image evaluation device, comprising:
   the spectral characteristic acquisition device as claimed in claim 1; and
   an image evaluation part configured to evaluate an image formed on the object based on a spectral characteristic of the object acquired by the spectral characteristic acquisition device.

10. An image formation apparatus, comprising:
    an image formation device configured to form an image on the object; and
    the image evaluation device as claimed in claim 9.

\* \* \* \* \*